(12) United States Patent
Yamada et al.

(10) Patent No.: US 7,875,447 B2
(45) Date of Patent: Jan. 25, 2011

(54) CELL INCUBATOR FOR SINGLE CELL OPERATION SUPPORTING ROBOT

(75) Inventors: Yohei Yamada, Tokyo (JP); Mikako Saito, Tokyo (JP); Hideaki Matsuoka, Tokyo (JP)

(73) Assignees: Chuo Precision Industrial Co., Ltd., Tokyo (JP); Tokyo University of Agriculture and Technology National University Corporation, Tokyo (JP)

( * ) Notice: Subject to any disclaimer, the term of this patent is extended or adjusted under 35 U.S.C. 154(b) by 109 days.

(21) Appl. No.: 11/577,006

(22) PCT Filed: Aug. 2, 2005

(86) PCT No.: PCT/JP2005/014080

§ 371 (c)(1),
(2), (4) Date: Apr. 11, 2007

(87) PCT Pub. No.: WO2006/040870

PCT Pub. Date: Apr. 20, 2006

(65) Prior Publication Data

US 2008/0014628 A1    Jan. 17, 2008

(30) Foreign Application Priority Data

Oct. 12, 2004    (JP) .............................. 2004-298133

(51) Int. Cl.
*C12M 1/00* (2006.01)
(52) U.S. Cl. .............. 435/287.1; 435/287.2; 435/287.3; 356/244
(58) Field of Classification Search ... 435/287.1–287.3; 356/244
See application file for complete search history.

(56) References Cited

U.S. PATENT DOCUMENTS

| 3,829,216 | A | * | 8/1974 | Persidsky ..................... 435/39 |
| 4,589,743 | A | * | 5/1986 | Clegg .......................... 359/398 |
| 5,766,677 | A | * | 6/1998 | Dimou et al. ............... 427/166 |
| 2004/0092001 | A1 | * | 5/2004 | Bedingham et al. ...... 435/286.2 |

(Continued)

FOREIGN PATENT DOCUMENTS

EP    1544286    6/2005

(Continued)

OTHER PUBLICATIONS

English Language Abstract of JP 10-217163.

(Continued)

*Primary Examiner*—Michael A Marcheschi
*Assistant Examiner*—Jameson Q Ma
(74) *Attorney, Agent, or Firm*—Greenblum & Bernstein, P.L.C.

(57) ABSTRACT

To provide an inexpensive cell incubator for a single cell operation supporting robot having the markers (first and second feature points) required to transform the position of a cell detected on a table coordinate system into a position on the intrinsic coordinate system of the cell incubator. First and second feature points are formed on a film-like feature point setup chip which is then stuck to the cell incubator body such as a conventional dish, thus constituting a cell incubator. Since manufacture of a new die for forming the first and second feature points directly on the cell incubator body is not required, an inexpensive cell incubator for a single cell operation supporting robot can be provided.

2 Claims, 17 Drawing Sheets

U.S. PATENT DOCUMENTS

2005/0254046 A1 11/2005 Matsuoka et al.

FOREIGN PATENT DOCUMENTS

| JP | 5-49467 | 3/1993 |
| JP | 5-322716 | 7/1993 |
| JP | 10-217163 | 8/1998 |
| JP | 2000-098258 | 4/2000 |
| JP | 2000-98258 | 4/2000 |
| JP | 2004-146203 | 5/2004 |
| JP | 2005-326341 | 11/2005 |
| WO | 02/46354 | 6/2002 |
| WO | 2004/015055 | 2/2004 |

OTHER PUBLICATIONS

English Language Abstract of JP 2000-098258.
English Language Abstract of JP 5-322716.
English Language Abstract of JP 2005-326341.
English Language Abstract of JP 2004-146203.

* cited by examiner

FIG. 11

| F \ A | 1 | 2 | 3 | 4 | 5 | · | · | · | · | · | · |
|---|---|---|---|---|---|---|---|---|---|---|---|
| 1 | ID NAME 1 | NUMBER 1 | (x3,y3) | (x4,y4) | (x5,y5) | · | · | · | (xi,yi) | · | · |
| 2 | ID NAME 2 | NUMBER 2 | (x3,y3) | (x4,y4) | (x5,y5) | · | · | · | (xi,yi) | · | · |
| 3 | ID NAME 3 | NUMBER 3 | (x3,y3) | (x4,y4) | (x5,y5) | · | (xi,yi) | · | — | · | · |
| 4 | ID NAME 4 | NUMBER 4 | (x3,y3) | (x4,y4) | (x5,y5) | · | · | · | (xi,yi) | · | · |
| · | · | · | · | · | · | · | · | · | · | · | · |
| · | · | · | · | · | · | · | · | · | · | · | · |
| · | · | · | · | · | · | · | · | · | · | · | · |
| m | ID NAME m | NUMBER m | (x3,y3) | (x4,y4) | · | · | · | (xi,yi) | · | · | · |

FIG. 18
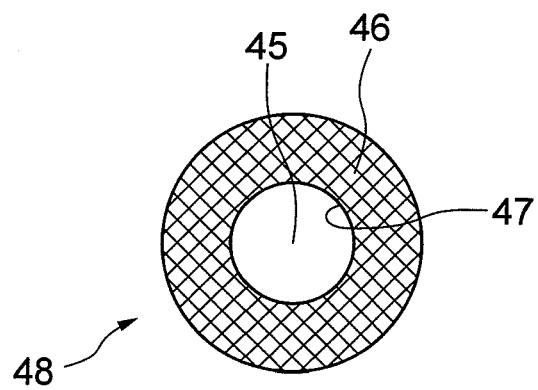
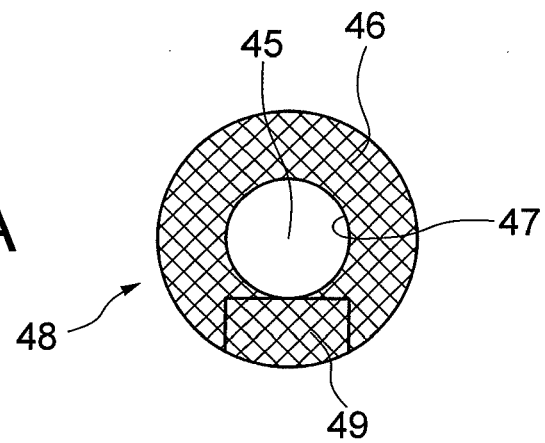
FIG. 19A
FIG. 19B
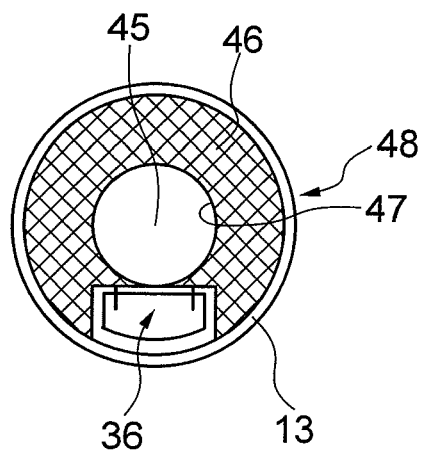

CELL INCUBATOR FOR SINGLE CELL OPERATION SUPPORTING ROBOT

TECHNICAL FIELD

The present invention relates to improvements in a cell incubator for a single cell operation supporting robot, which comprises a first and a second feature points used as markers when transforming the position of a cell that is detected on a table coordinate system of the single cell operation supporting robot into the position on an intrinsic coordinate system of the incubator.

BACKGROUND ART

There is a single cell operation supporting robot already known as Patent Literature 1, in which a table that moves on a horizontal plane and two manipulators that are capable of moving in three-axial directions are mounted so as to carry out operations such as holing, moving, and injection targeted on individual cells within a cell incubator placed on the table.

However, this single cell operation supporting robot is basically designed for the case of using a micro-well that individually stores the single cell. Therefore, it has sometimes been difficult to teach and store the positions of each cell properly to the robot, when the single cells are dispersedly disposed in a disordered manner within the cell incubator.

Further, even if a micro-well is used, the position and posture of the cell incubator with respect to the table are changed when the incubator itself is detached and then placed on the table again. Thus, it becomes difficult to carry out a proper processing operation if the position data of each cell provided in the past is used as it is.

In order to overcome this kind of issues, the Applicants of the present invention have already proposed Japanese Patent Unexamined Publication 2004-146203. Disclosed therein are a cell position teaching method and a single cell operation supporting robot, which: obtain a transformation matrix for transforming a table coordinate system into a dish coordinate system through utilizing a first and a second feature points formed on a dish serving as a cell incubator, and utilizing a function of the single cell operation supporting robot itself provided for detecting the current positions at each axis on a table; obtain positions of each cell on the dish coordinate system by multiplying the transformation matrix to the position of each cell detected on the basis of the table coordinate system; and the positions of those cells are registered to a file by being associated with identification names for specifying the dish. Also disclosed therein is a dish for a single cell operation supporting robot, which comprises the first and second feature points to be used in the single cell operation supporting robot described above.

However, for the dish for a single cell operation supporting robot proposed in Japanese Patent Unexamined Publication 2004-146203, it is assumed basically that the first and second feature points are formed integrally with the dish that serves as the cell incubator. Thus, it is necessary to create a new die for molding the dish that comprises protrusions or concaves for forming the first and second feature points on the bottom face of the dish. Therefore, there still remains such an issue that the cost for manufacturing the dishes becomes high.

Further, in order to detect the positions of the first and second feature points on the table coordinate system, it is necessary to locate those feature points at specific positions in the view field of a microscope. However, the line width of the long segment and the short segments which form the first and second feature points is as thin as 5 µm or less. Therefore, it is sometimes difficult to locate those feature points within the view field of the microscope or in the vicinity thereof at the preparatory stage. In such a case, it is required to find the feature points by searching the bottom face of the dish thoroughly with the microscope for teaching the posture of the dish. As a result, there may cause such an inconveniences that the time for the preparatory work is extended.

Patent Literature 1: WO publication 2004/015055 A1 Pamphlet (FIG. 1, FIG. 3)

DISCLOSURE OF THE INVENTION

The object of the present invention therefore is to provide, at a low cost, a cell incubator for the single cell operation supporting robot, which is capable of setting the first and second feature points in the view field of a microscope without searching the entire bottom face of the cell incubator such as a dish by a microscope, without requiring a new die for manufacturing the cell incubator such as the dish.

The present invention is a cell incubator used for a single cell operation supporting robot where: a cell incubator having cells placed thereon is loaded on a table; position of a first feature point provided to the cell incubator and position of a second feature point provided to the cell incubator are detected on a table coordinate system; there is obtained a transformation matrix for matching a first axis of the table coordinate system with a straight line that starts from the first feature point and passes through the second feature point; and there is obtained a cell position on an intrinsic coordinate system of the cell incubator by multiplying the transformation matrix to each cell position detected on the table coordinate system. In order to overcome the aforementioned issues, the cell incubator comprises a cell incubator main body for placing cells, and a film-like feature point setup chip on which the first and second feature points are formed, wherein the feature point setup chip is stuck to the cell incubator main body.

By constituting the cell incubator for the single cell operation supporting robot through forming the first, second feature points on the film-like feature point setup chip, and sticking the feature point setup chip to the cell incubator main body, it is possible to provide, at a low cost, a cell incubator for the single cell operation supporting robot provided with the markers that are required for transforming the position of the cell detected on the table coordinate system into a position on the intrinsic coordinate system of the cell incubator, without fabricating a new die for forming the first, second feature points directly on the cell incubator main body.

Furthermore, since the existing dishes, flask plates, the slide glasses, or the like can be used as the cell incubator main bodies, users can freely select and use the accustomed cell incubator main body that has been used conventionally or various kinds of cell incubator main bodies appropriate for the objective of the experiments and the like, i.e. freely select and use the dishes, the flask plates, the slide glasses, etc.

Moreover, since the feature point setup chip has a thickness of some extent, the stuck position of the feature point setup chip on the cell incubator main body i.e. the position where the first and second feature points are placed, can easily be recognized visually. Through the visual inspection, the cell incubator can be placed on the table by setting the positions of the first, second feature points within the view field of the microscope or in the vicinity thereof. As a result, it becomes unnecessary to find the feature points by searching the entire bottom face of the cell incubator with the microscope. Therefore, the work time for preparation can be saved.

As the processing techniques for forming the first and second feature points on the film-like feature point setup chip, it is possible to use various known techniques such as laser sputtering, printing, caving, or the like. Furthermore, as the materials for the feature point setup chip, it is possible to use glass, quartz, resin, or the like.

Further, at least a part of a circumferential contour of the feature point setup chip may be formed to match a circumferential contour shape of a bottom face of the cell incubator main body that is a target for sticking the feature point setup chip.

As described, through forming the circumferential contour of the feature point setup chip to match the shape of the circumferential contour of the bottom face of the cell incubator main body, the position setting work when sticking the feature point setup chip to the cell incubator main body becomes easy. In particular, when manufacturing a great number of same-kind cell incubators in the same shape and size for the single cell operation supporting robot, it is possible to prevent variations generated in the sticking position of the feature point setup chips.

For example, if the outer diameter of the bottom face of the dish used as the cell incubator main body is 30 mm$\phi$, a part of the circumferential contour of the feature point setup chip is formed in an arc shape of 30 mm$\phi$, and it is stuck by having the circumferential contour along the circumferential contour of bottom face of the cell incubator main body. With this, the sticking position of the feature point setup chip to the cell incubator main body can be specified.

Further, a corner part may be formed at both sides of a straight-line side that constitutes a part of a circumferential contour of the feature point setup chip.

In the case of applying such structure, it is possible to prevent variations generated in the sticking positions of the feature point setup chips to the cell incubator main bodies, through sticking the feature point setup chip to the cell incubator main body (specifically, the one whose circumferential contour of the bottom face is circular, e.g. a dish) while having the corner parts positioned on both sides of the straight-line side inscribed to the circumferential contour of the bottom face of the cell incubator main body.

It is desirable to form the two feature points by the intersection points between a long segment and each of short segments which are substantially orthogonal to the long segment at both ends.

As described above, the feature point setup chip has a thickness of some extent, so that the stuck position of the feature point setup chip on the cell incubator main body i.e. the position where the first and second feature points are placed, can easily be recognized visually, and the cell incubator can be placed on the table by setting the positions of the first, second feature points within the view field of the microscope or in the vicinity thereof. Therefore, the line width of the long segment and the short segments which constitute the feature points can be formed as narrow as possible within a detectable range. With this, the position detecting accuracy of the feature points and, further, the teaching accuracy of the cell positions can be improved.

Furthermore, a blank part for covering at least a part of a bottom face of the cell incubator is desirable to be formed in the feature point setup chip. In the blank part, a boundary display part, which clarifies a boundary between a safe moving zone where movement of the table is tolerated without generating interference between the single cell operation supporting robot as well as additional devices thereof and the cell incubator, and a danger zone where interference may be generated between the single cell operation supporting robot as well as additional devices thereof and the cell incubator due to the movement of the table, is provided to be identifiable from the view field of a microscope of the single cell operation supporting robot.

Through providing the boundary display part for clarifying the boundary between the safe moving zone and the danger zone at the blank part in the feature point setup chip, table moving work carried out by manual operation can be rapidly and safely performed. That is, there is no interference generated between the single cell operation supporting robot as well as the additional devices thereof and the cell incubator, unless the view field of the microscope goes over the boundary display part and enters the danger zone. Therefore, the operator can move the table freely within this range while keeping eyes on the microscope.

Therefore, the operator can be relieved from a troublesome work such as moving the table nervously while checking the clearance between the single cell operation supporting robot as well as the additional devices thereof and the cell incubator by taking eyes off from the microscope every time. In particular, there is an advantage of achieving a dramatic cut in the time that is required for the initial teaching operation, e.g. teaching the positions of the dispersed single cells on the incubator by selecting the cells one by one with manual operation.

The boundary display part is preferable to be formed by a boundary line on an inner side of a masking part which clarifies the danger zone, for example.

When applying such structure, the safe moving zone and the danger zone can be distinguished as planes. Therefore, compared to the case where the safe moving zone and the danger zone are distinguished by a simple boundary line with no area, it is possible to perform manual operation of the table by easily and securely discriminating the safe moving zone and the danger zone. In particular, it becomes possible to securely prevent such an operational mistake that the view field of the microscope goes over the boundary display part and imprudently enters the danger zone.

More specifically, as the masking part for clarifying the danger zone, it is possible to use a black light shield part that shields the passage of light, a colored semitransparent part that gives a color to the observation light from the underneath the cell incubator, a mat face or opalescent part or the like, which diffuses the light. When the masking part is formed with the black light shield part or the like for shielding the passage of the light, it is impossible to observe this zone by the microscope. Therefore, when the operator tries to bring the view field of the microscope into this zone, it is denied with strong motives. As a result, mis-operations can be prevented more securely.

The part on the inner side of the boundary line of the masking part is the safe moving zone, and the operator sets the cells within the view field of the microscope within this range. Thus, this zone is formed transparent or formed as a cutout part. When it is formed as a cutout part, this zone does not function as a blank part of the feature point setup chip. However, the boundary display part is formed with the boundary line on the inner side of the masking part for clarifying the danger zone. Therefore, it makes no difference that the masking part and the boundary display part are provided in the blank part of the feature point setup chip.

The cell incubator for the single cell operation supporting robot according to the present invention is constituted through forming the first, second feature points on the film-like feature point setup chip, and sticking the feature point setup chip to the cell incubator main body. Thus, it is possible to provide, at a low cost, a cell incubator for the single cell operation supporting robot provided with the markers (the first and second feature points) that are required for transforming the position of the cell detected on the table coordinate system into a position on the intrinsic coordinate system of the cell incubator, without fabricating a new die for forming the first, second feature points directly on the cell incubator main body.

Furthermore, since the existing dishes, flask plates, the slide glasses, or the like can be used as the cell incubators, users can freely select and use the accustomed cell incubator main body that has been used conventionally or various kinds of cell incubator main bodies appropriate for the objective of the experiments and the like, i.e. freely select and use the dishes, the flask plates, the slide glasses, etc.

Moreover, since the feature point setup chip has a thickness of some extent, the stuck position of the feature point setup chip on the cell incubator main body i.e. the position where the first and second feature points are placed, can easily be recognized visually. Through the visual inspection, the cell incubator can be placed on the table by setting the positions of the first, second feature points within the view field of the microscope or in the vicinity thereof. As a result, it becomes unnecessary to find the feature points by searching the entire bottom face of the cell incubator with the microscope. Therefore, the work time for preparation can be saved.

Furthermore, since at least a part of a circumferential contour of the feature point setup chip is formed to match a circumferential contour shape of a bottom face of the cell incubator main body, the position setting work when sticking the feature point setup chip to the cell incubator main body becomes easy. In the case where a great number of same-kind cell incubators in the same shape and size for the single cell operation supporting robot are manufactured, it is possible to prevent generation of individual differences in the cell incubators, i.e. prevent variations generated in the sticking position of the feature point setup chips beforehand.

Further, in the case where a corner part is formed at both sides of a straight-line side that constitutes a part of a circumferential contour of the feature point setup chip, it is possible to prevent generation of individual differences in the cell incubators, i.e. prevent variations generated in the sticking positions of the feature point setup chips to the cell incubator main bodies, through sticking the feature point setup chip to the cell incubator main body while having the corner parts inscribed to the circumferential contour of the bottom face of the cell incubator main body.

Particularly, in the case where the two feature points on the feature point setup chip are formed by the intersection points between a long segment and each of short segments which are substantially orthogonal to the long segment at both ends, the stuck position of the feature point setup chip on the cell incubator main body i.e. the position where the first and second feature points are placed, can easily be recognized visually, and the cell incubator can be placed on the table by setting the positions of the first, second feature points within the view field of the microscope or in the vicinity thereof. Therefore, the line width of the long segment and the short segments which constitute the feature points can be formed as narrow as possible within a detectable range. With this, the position detecting accuracy of the feature points and, further, the teaching accuracy of the cell positions can be improved.

Furthermore, a blank part for covering at least a part of the bottom face of the cell incubator is formed in the feature point setup chip. In the blank part, a boundary display part, which clarifies a boundary between a safe moving zone where movement of the table is tolerated without generating interference between the single cell operation supporting robot as well as additional devices thereof and the cell incubator, and a danger zone where interference may be generated between the single cell operation supporting robot as well as additional devices thereof and the cell incubator due to the movement of the table, is provided to be identifiable from the view field of a microscope. Therefore, through operating the table in such a manner that the view field of the microscope does not go over and enter the danger zone, interference between the single cell operation supporting robot as well as the additional devices thereof and the cell incubator can be prevented securely. Therefore, the operator can be relieved from a troublesome work such as moving the table nervously while checking the clearance between the single cell operation supporting robot as well as the additional devices thereof and the cell incubator by taking eyes off from the microscope every time. Thus, the operator can perform the table moving work by the manual operation rapidly and safely, while keeping an eye on the microscope.

Particularly, when forming the boundary display part with the boundary line on the inner side of the masking part for clarifying the danger zone, the safe moving zone and the danger zone can be distinguished as planes. Therefore, compared to the case where the safe moving zone and the danger zone are distinguished by a simple boundary line with no area, it is possible to perform manual operation of the table by easily and securely discriminating the safe moving zone and the danger zone. Particularly, it becomes possible to securely prevent such an operational mistake that the view field of the microscope goes over the boundary display part and imprudently enters the danger zone.

BRIEF DESCRIPTION OF THE DRAWINGS

[FIG. 11] A conceptual diagram for showing an example of a data storage file to which the teaching positions of the single cells are stored;

[FIG. 15] A plan view for showing an example of the structural elements of the cell incubator for a single cell operation supporting robot, in which

[FIG. 16] A plan view for showing another example of structural elements of the cell incubator for a single cell operation supporting robot, in which

[FIG. 18] A plan view for showing an example of an interference preventing chip which prevents the interference generated between the single cell operation supporting robot as well as the additional devices thereof and the cell incubator;

[FIG. 19] A plan view for showing an example of an interference preventing chip that can be used together with the feature point setup chip, in which FIG. 19A shows the structure of the interference preventing chip, and FIG. 19B shows the dish to which the feature point setup chip and the interference preventing chip are stuck;

[FIG. 21] A plan view for showing another structural example of the cell incubator for a single cell operation supporting robot, in which

BEST MODE FOR CARRYING OUT THE INVENTION

First, there is described a specific example of a single cell operation supporting robot (the one disclosed in Japanese Unexamined Patent Publication 2004-146203) that uses an incubator of the present invention.

Figure 1:
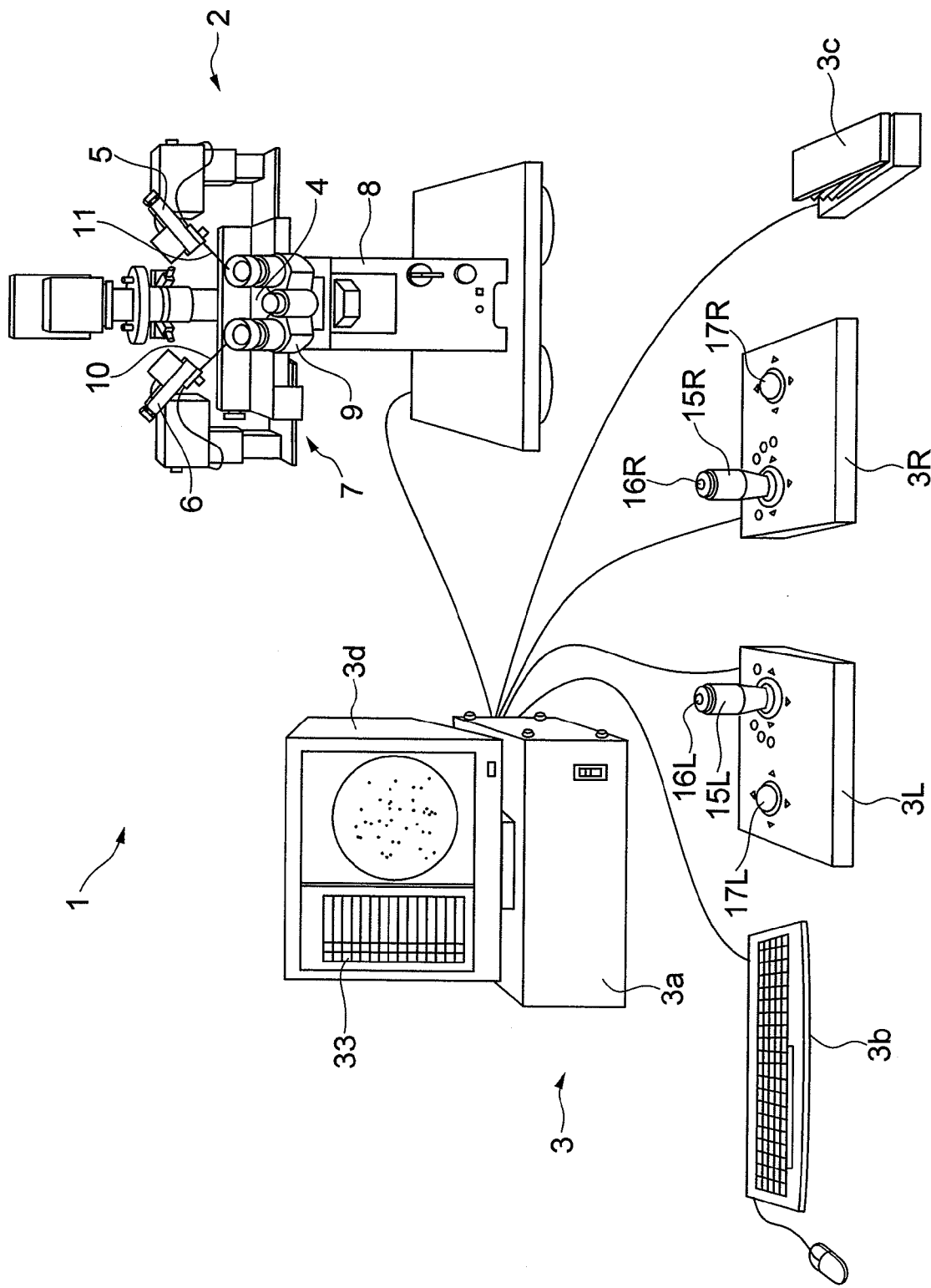
[FIG. 1] A front elevational view for showing the overall structure of a single cell operation supporting robot.

FIG. 1 is a front elevational view for showing the overall structure of a single cell operation supporting robot 1. As shown in FIG. 1, the single cell operation supporting robot 1 is constituted roughly with a robot main body 2 and a controller 3.

Among those, the robot main body 2 comprises: a table 4 for loading a cell incubator such as a dish; a stage 7 on which manipulators 5 and 6 for handling the cells within the cell incubator are mounted; a column 8 for supporting the stage 7; and a microscope 9 provided at a specific position on the table coordinate system in order to observe the cells within the cell incubator.

Figure 2:
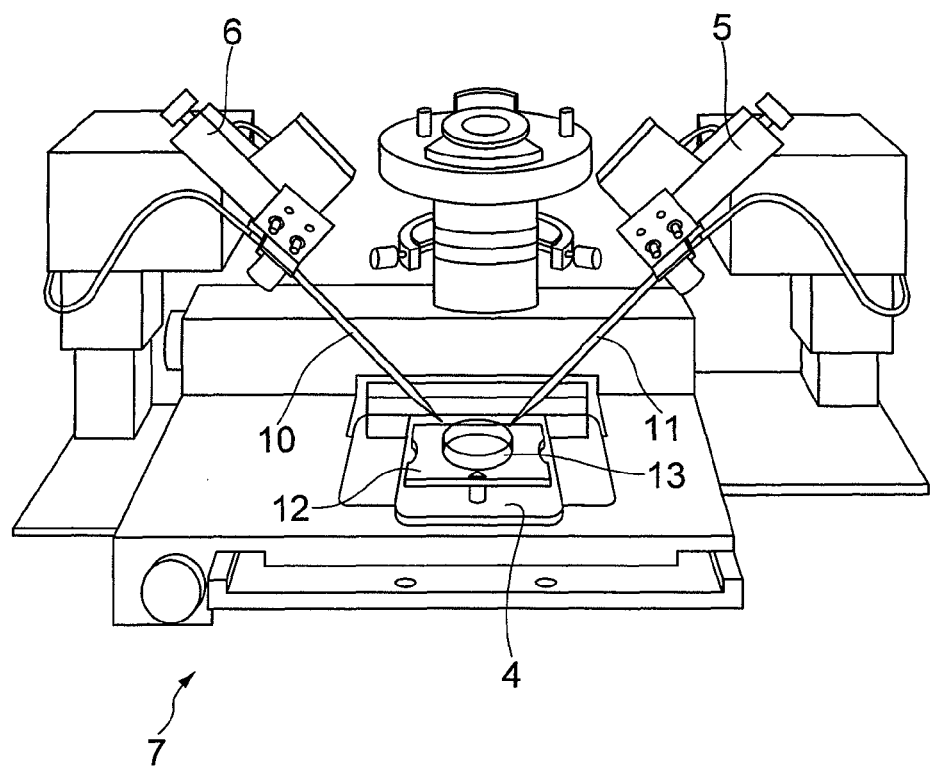
[FIG. 2] A front elevational view for showing an enlarged view of a stage of the single cell operation supporting robot.

FIG. 2 shows the structure of the stage 7. The table 4 provided on the stage 7 is driven on a horizontal plane of orthogonal two axes by driving devices X1 and X2 of each axis, which are constituted with a stepping motor and the like. Further, the manipulator 5 arranged on the right side of the table 4 is driven individually within a space of orthogonal three axes by driving devices XR and YR of each axis, which are constituted with a stepping motor and the like, as well as a driving device ZR that is constituted with a piezo-actuator or the like. The manipulator 6 arranged on the left side of the table 4 is driven individually within a space of orthogonal three axes by driving devices XL, YL, and ZL of each axis, which are constituted with a stepping motor and the like. However, the course of direction of the Z-axis of the manipulators 5 and 6 is set at 45 degrees with respect to the horizontal plane so as not to block the view field of the microscope 9.

Among those, the manipulator 6 arranged on the left side of the table 4 comprises a capillary 10 as an end effecter for holding the single cell disposed within the cell incubator by means of suction or the like. Further, the manipulator 5 arranged on the right side of the table 4 comprises, as an end effecter, a capillary 11 having an injection hole at the end thereof for injecting a gene, a chemical, or the like into a single cell.

Further, an incubator holder 12 is fixed to the table 4 for setting the rough position when placing the incubator, and a dish 13, which is a type of the incubator, is loaded on the table 4 through the incubator holder 12.

Figure 3:
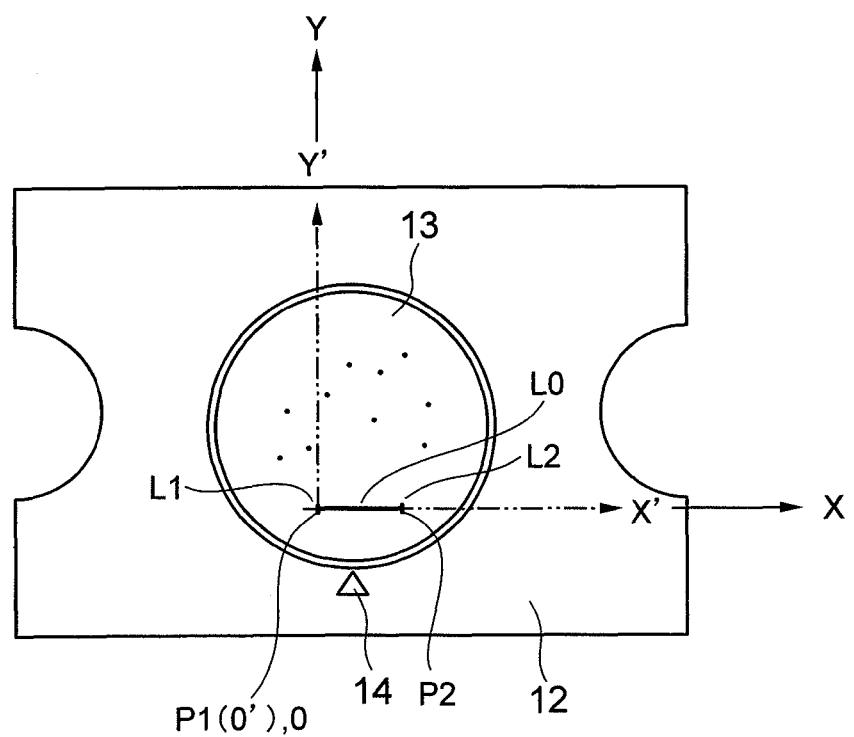
[FIG. 3] A plan view for showing the appearance of a dish as a kind of cell incubators.

FIG. 3 shows a plan view of the appearance of the dish 13. The dish 13 is a flat-bottom container made of glass or plastic, and two feature points P1 and P2 are provided at the bottom face thereof. Specifically, these feature points P1 and P2 are formed by the intersection points between a long segment L0 positioned at the bottom face of the dish 13 and each of short segments L1, L2 which are substantially orthogonal to the long segment L0 at both ends.

These feature points P1 and P2 are used for defining the dish coordinate system that is intrinsic to the dish 13, and for specifying the position and posture of the dish 13 with respect to the table coordinate system.

The coordinate system intrinsic to the dish 13 is defined on condition that a straight line that starts from the first feature point P1 and passes through the second feature point P2 as a first axis (X'-axis), and an orthogonal straight line with respect to that straight line, which passes through the first feature point P1, as a second axis (Y'-axis). An example of the dish coordinate system that is intrinsic to the dish 13 is shown in FIG. 3 with an alternate long and two short dash line.

A marking 14 as shown in FIG. 3 is provided to the incubator holder 12. Through attaching the dish 13 by aligning the center area of the long segment L0 with the tip of the marking 14, the coordinate origin O' of the dish coordinate system is almost matched with the coordinate origin O of the table coordinate system, while the first axis (X'-axis) of the dish coordinate system is matched substantially with the first axis (X-axis) of the table coordinate system. However, it does not change the fact that the dish 13 is set by handwork. Thus, the both may not necessarily be matched in a strict manner, and the marking 14 merely helps to give estimation.

The coordinate origin O of the table coordinate system herein is not the origin of a machine on hardware that corresponds to a stroke end of the table 4 but the coordinate origin in terms of drive control. Therefore, in practice, the coordinate origin O of the table coordinate system may be defined at any positions within a movable range of the table 4. Further, the coordinate origin O' of the dish coordinate system is matched with the first feature point P1 in the case of FIG. 3. In practice, however, the coordinate origin O' of the dish coordinate system is not necessarily matched with the first feature point P1, either. It may be defined at a position being offset from the first feature point P1 in the directions of the first axis (X'-axis) and the second axis (Y'-axis) of the dish coordinate system, since the offset amount can be dealt at the stage of arithmetic processing as a constant term. For simplifying the explanation, it is assumed herein that the coordinate origin O' of the dish coordinate system is defined to match with the first feature point P1.

The first and second feature points P1 and P2 formed by the intersection points between the long segment L0 and the short segments L1, L2 are provided at the positions closer to the circumference of the bottom face of the dish 13 so as not to interrupt the loading of the single cells in the dish 13, by considering the effective use of the area of the dish 13. For securing the detection accuracy of the position and the posture of the dish 13 by using the feature points P1 and P2, it is necessary for the line width of the long segment L0 and the short segments L1, L2 to be 5 μm or less, and it is more desirable to be 3 μm or less. This allows the substantial area of the feature points P1 and P2 to be narrowed remarkably, thereby enabling the specifying accuracy of the feature positions to be improved dramatically compared to the case of the typical marker using a dot or the like. Detecting work of the feature points P1 and P2 is performed by using the microscope 9 fixed to the robot main body 2. Thus, detection of the feature points P1 and P2 does not become difficult, even if the line width of the long segment L0 and the short segments L1, L2 is narrowed. Therefore, it is desirable to narrow the line width as much as possible within a technically possible range.

The main part of the controller 3 for drive-controlling each part of the single cell operation supporting robot 1 is constituted with a controller main body 3a. A first operation board 3R, a second operation board 3L, a keyboard 3b with a mouse a foot switch 3c, and a monitor 3d, which function as the man-machine interfaces, are connected to the controller main body 3a.

The first operation board 3R is a manual operation device for alternatively drive-controlling the table 4 or the manipulator 5 provided on the right side thereof, and it is possible to select whether to control the table 4 or the manipulator 5 by operating a head switch 16R provided at the top of a joystick 15R. Movements of the table 4 and the manipulator 5 on the horizontal plane are controlled through the joystick 15R or a trackball 17R. Movements of the capillary 11 as the end effecter of the manipulator 5 in the inserting direction (Z-axis direction) are controlled through a rotary operation of the top of the joystick 15R.

The second operation board 3L is a manual operation device for drive-controlling the manipulator 6 provided on the left side of the table 4. Movements of the manipulator 6 within the horizontal plane are controlled through a joystick 15L or a trackball 17L. Movements of the capillary 10 as the end effecter of the manipulator 6 in the Z-axis direction are controlled through a rotary operation of the top of the joystick 15L.

Figure 4:
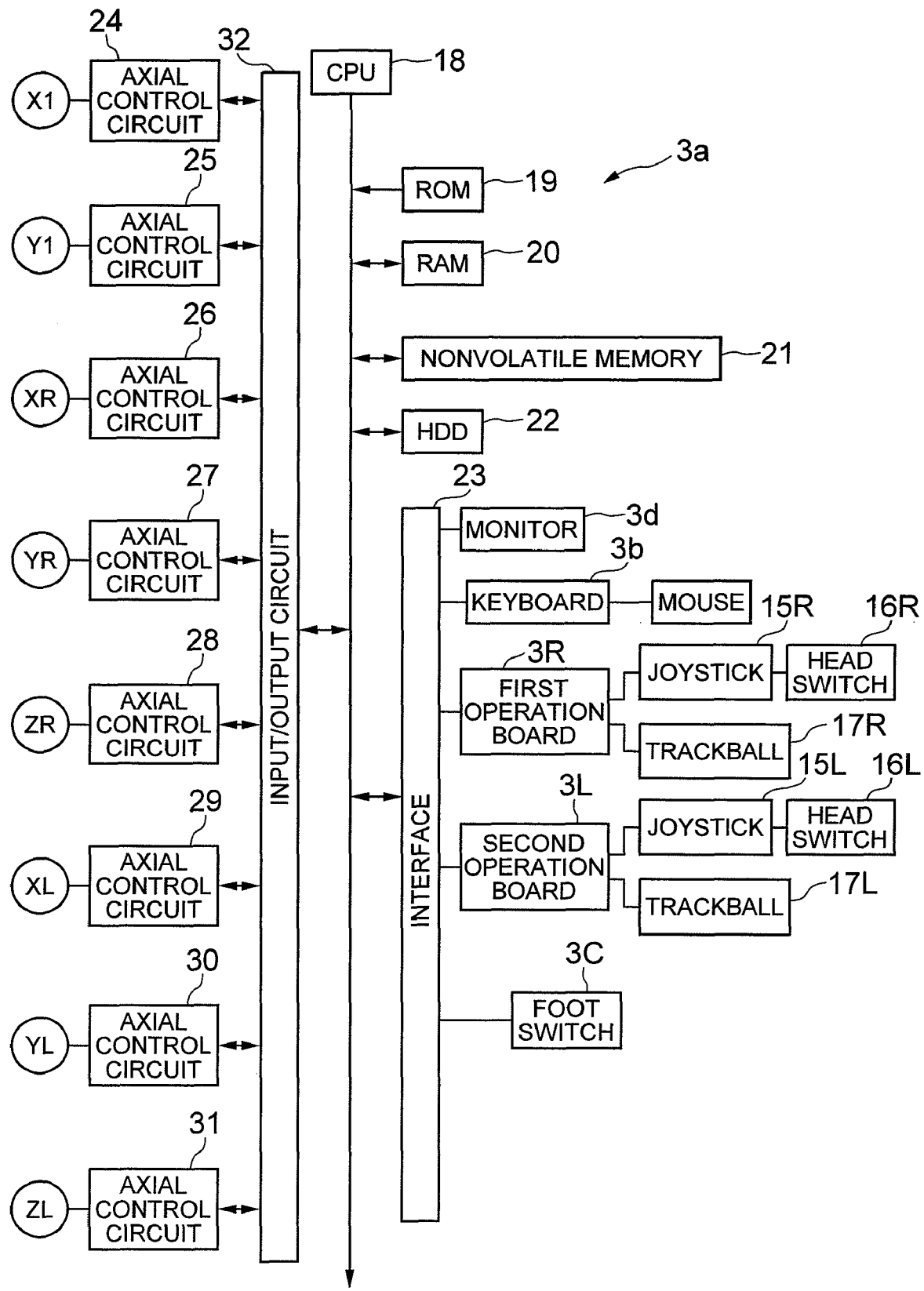
[FIG. 4] A functional block diagram for showing the schematic structure of a controller main body.

FIG. 4 is a functional block diagram for showing the schematic structure of the controller main body 3a. The main part of the controller main body 3a is constituted with: a CPU 18 for drive-controlling each part of the single cell operation supporting robot 1; a ROM 19 where a drive-control program of the CPU 18 is stored; a RAM 20 used for temporal storage and the like of the arithmetic data; a nonvolatile memory 21 which functions as a current position storage register, a parameter storage device, and the like; and a hard disk drive 22 and the like for storing files and the like of teaching data regarding the cell positions.

Operation signals from the joystick 15R, the head switch 16R, the trackball 17R, which are provided on the first operation board 3R, operation signals from the joystick 15L, the head switch 16L, the trackball 17L, which are provided on the second operation board 3L, and signals from the keyboard 3b and the mouse thereof as well as the foot switch 3c are inputted to the CPU 18 through the interface 23. Further, display signals from the CPU 18 are inputted to the monitor 3d through the interface 23.

The driving devices X1, Y1 at each axis on the table 4, the driving devices XR, YR, ZR at each axis of the manipulator 5, and the driving devices XL, YL, ZL at each axis of the manipulator 6 are drive-controlled through axial control circuits 24, 25, 26, 27, 28, 29, 30, 31 for each axis and an input/output circuit 32.

Figure 5:
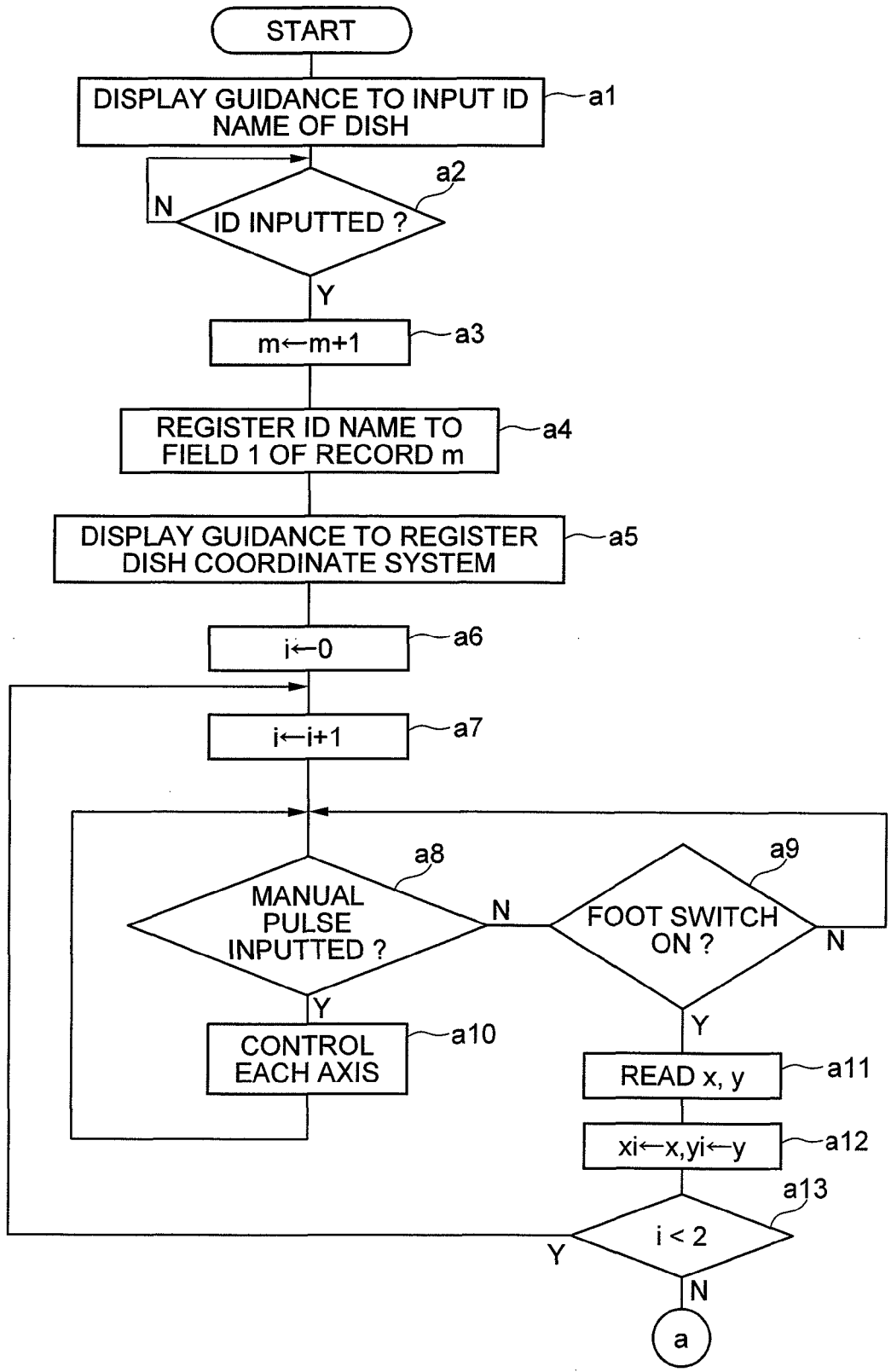
[FIG. 5] A flowchart of the cell position teaching processing executed by a CPU of the controller main body.
Figure 6:
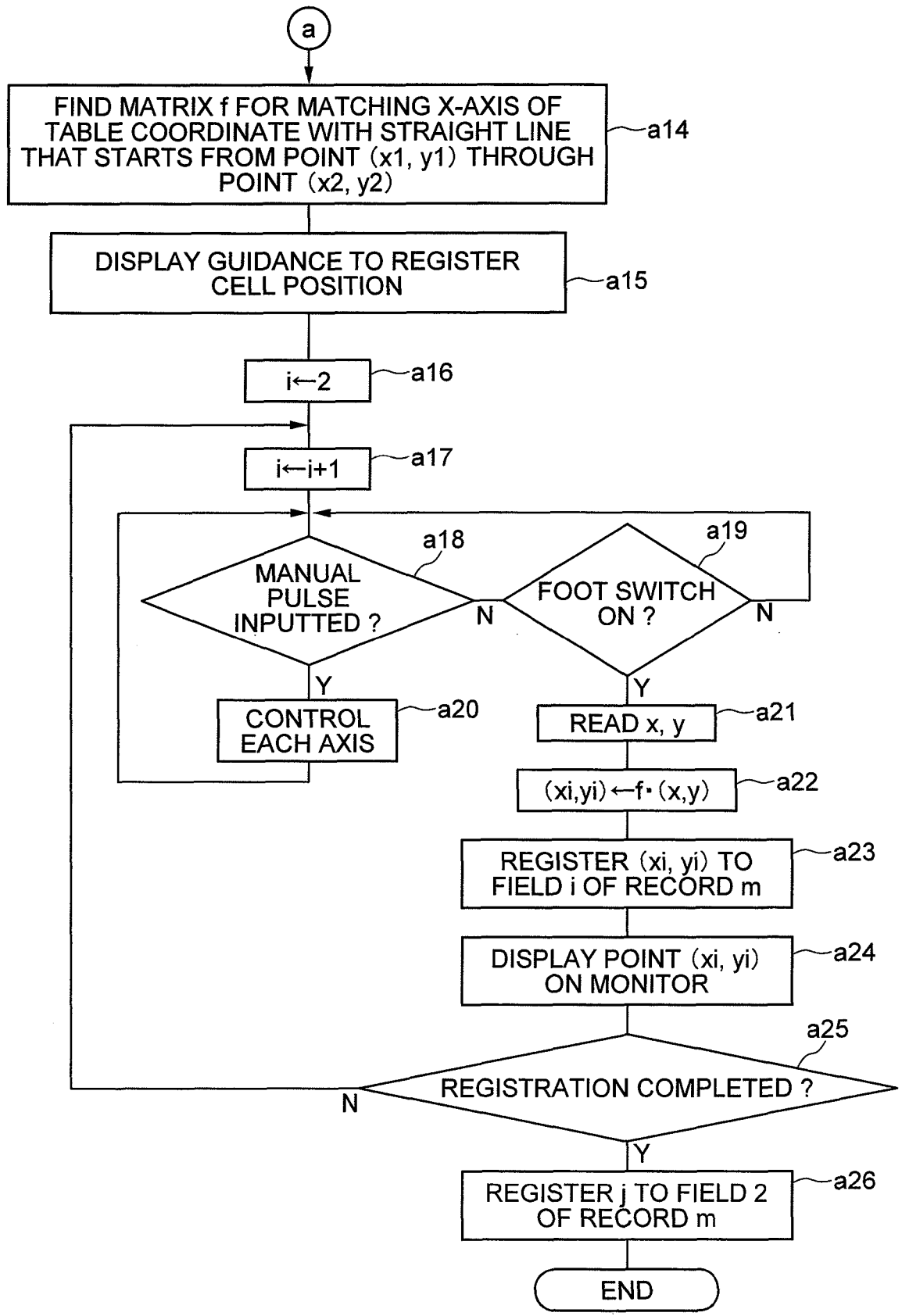
[FIG. 6] A following flowchart of the cell position teaching processing.
Figure 7:
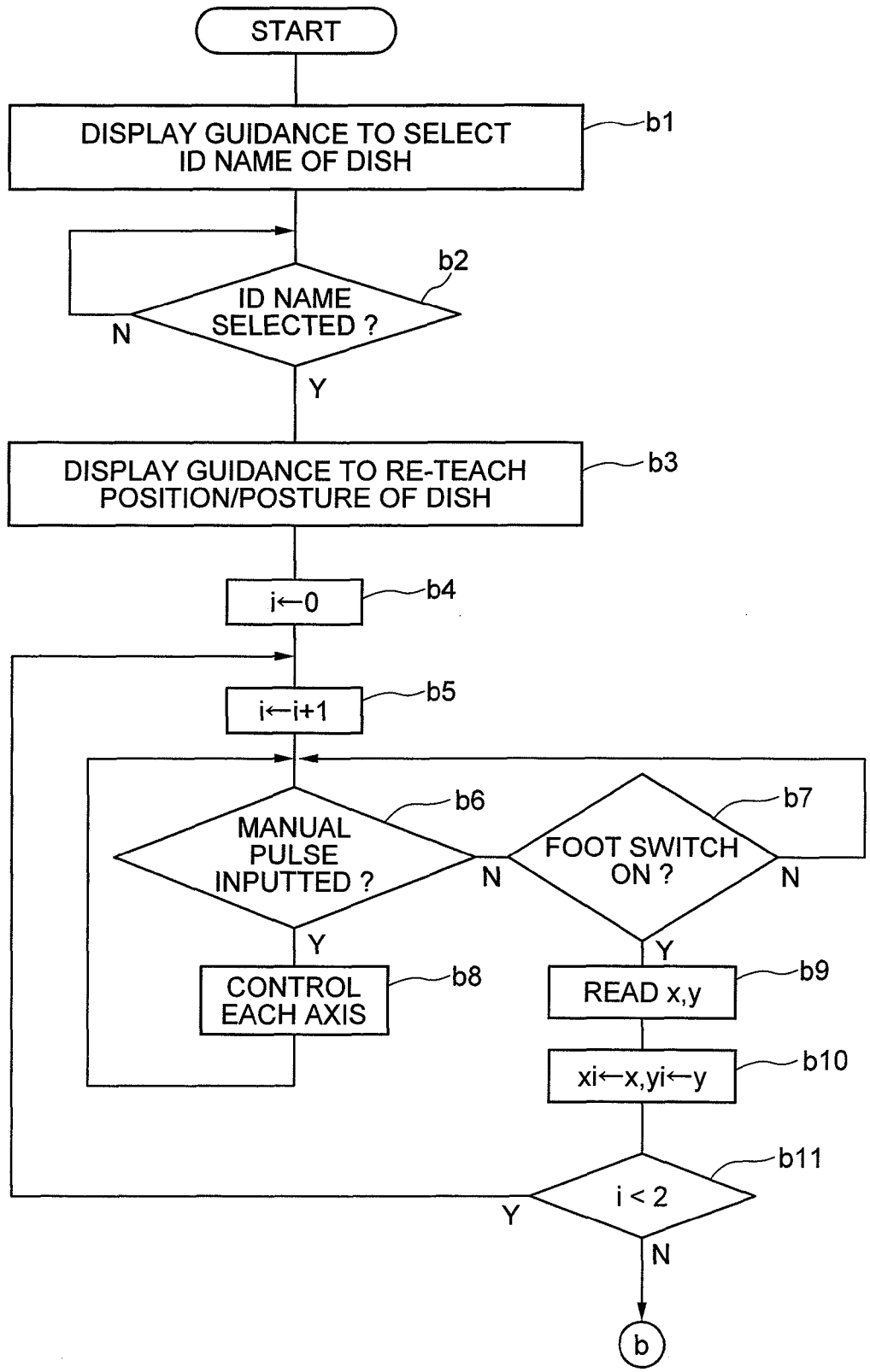
[FIG. 7] A flowchart of the playback processing executed by the CPU of the controller main body.

FIG. 5 and FIG. 6 are flowcharts for illustrating the outline of the cell position teaching processing executed by the CPU 18 of the controller main body 3a. Further, FIG. 7-FIG. 10 are flowcharts for illustrating the outline of the playback processing executed by the CPU 18.

First, when the dish 13 where single cells are dispersedly disposed is loaded on the table 4 for the first time, the operator starts the controller main body 3a in a cell position teaching mode, and starts the cell position teaching processing as shown in FIG. 5 and FIG. 6 by the CPU 18.

When the dish 13 is loaded on the table 4 for the first time, as shown in FIG. 3, it is desirable to load it by matching the middle point of the long segment L0 of the dish 13 with the marking 14 of the incubator holder 12. Practically, however, a position shift and a posture change of some extent are to be generated.

The CPU 18 that has started the cell position teaching processing displays a message first on the monitor 3d for guiding the operator to input an identification name required for specifying the dish (step a1), and comes under a standby state to wait for an input operation of the operator (step a2).

When the operator operates the keyboard 3b to input an arbitrary identification name, the CPU 18 detects the input of the identification name by the judging processing of step a2. After incrementing the value of the register m for storing the number of registered identification names by 1 (step a3), the identification name inputted this time is registered additionally to the first field of the m-th record of the data storage file as shown in FIG. 11, which is built within the hard disk drive 22, based on the current value of the register m (step a4).

Then, the CPU 18 displays a message on the monitor 3d to guide the operator to register the dish coordinate system (step a5), and initializes the value of the index i for designating the register to store the positions of the feature points to 0 once (step a6). After incrementing the value of the index i again by 1 (step a7), the CPU 18 comes under a standby state to wait for a manual pulse from the first operation board 3R that functions as the manual operation device of the table 4 (step a8) or to wait for a dish posture teaching instruction inputted by the operator from the foot switch 3c (step a9).

The operator first operates the joystick 15R or the trackball 17R of the first operation board 3R that functions as the manual operation device so as to move the table 4 on which the dish 13 is loaded on the horizontal plane, in order to set the position of the first feature point P1 provided on the bottom face of the dish 13 at the center of the view field (center of the reticle) of the microscope 9.

The manual pulses outputted from the first operation board 3R according to the operation of the joystick 15R or the trackball 17R are detected by the CPU 18 by the processing of step a8. Upon this, the CPU 18 starts the driving devices X1 and Y1 in accordance with the inputted pulse number (step a10) to move the table 4 to the position desired by the operator.

Then, when the operator, who has captured the feature point P1 provided on the bottom face of the dish 13 at the center of the view field of the microscope 9, operates the foot switch 3c, the dish posture teaching instruction is outputted from the foot switch 3c, and this signal is detected by the CPU 18 by the processing of step a9.

Upon detecting the input of the dish posture teaching instruction, the CPU 18 reads the current positions of each axis on the table 4, i.e. the current position x of the first axis (X-axis) of the table coordinate system and the current position y of the second axis (Y-axis) of the table coordinate system, from the current position storage registers that correspond to the driving devices X1 and Y1 (step a11), and stores those values to each of the registers x1 and y1 temporarily based on the current values of the index i (step a12).

Then, the CPU 18 judges whether or not the current values of the index i have reached 2, i.e. whether or not the detecting work of the positions of the two feature points P1 and P2 have been completed (step a13). At this point, it still remains as i=1, indicating that the detecting work of the second feature point P2 has not ended yet. Therefore, the CPU 18 increments the value of the index i again by 1 (step a7) and, as described above, comes under a standby state to wait for the input of the manual pulse from the first operation board 3R (step a8), or wait for the input of the second dish posture teaching instruction from the foot switch 3c (step a9).

Then, the operator operates again the joystick 15R or the trackball 17R of the first operation board 3R that functions as the manual operation device so as to move the table 4 on which the dish 13 is loaded on the horizontal plane, in order to set the position of the feature point P2 provided on the bottom face of the dish 13 at the center of the view field of the microscope 9.

The manual pulses outputted from the first operation board 3R according to the operation of the joystick 15R or the trackball 17R are detected by the CPU 18 by the processing of step a8. Upon this, the CPU 18 starts the driving devices X1 and Y1 in accordance with the inputted pulse number (step a10) to move the table 4 to the position desired by the operator.

Then, when the operator, who has captured the feature point P2 provided on the bottom face of the dish 13 at the center of the view field of the microscope 9, operates the foot switch 3c, the second dish posture teaching instruction is outputted from the foot switch 3c, and this signal is detected by the CPU 18 by the processing of step a9.

Upon detecting the input of the second dish posture teaching instruction, the CPU 18 reads the current positions of each axis on the table 4, i.e. the current position x of the first axis (X-axis) of the table coordinate system and the current position y of the second axis (Y-axis) of the table coordinate system, from the current position storage registers that correspond to the driving devices X1 and Y1 (step a11), and stores those values to each of the registers x2 and y2 temporarily based on the current values of the index i (step a12).

Then, the CPU 18 judges whether or not the current values of the index i have reached 2, i.e. whether or not the detecting work of the positions of the two feature points P1 and P2 have been completed (step a13). At this point, it has already turned as i=2, indicating that the position detecting work regarding the first feature point P1 and the second feature point P2 has ended. Therefore, the CPU 18 finds the transformation matrix f for matching the first axis (X-axis) of the table coordinate system with the straight line that starts from the point (x1, y1) and passes through the point (x2, y2), based on the values of the registers x1, y1, x2, and y2, i.e. based on the position (x1, y1) at each axis on the table 4 at the point where the first dish posture teaching instruction is inputted, and the position (x2, y2) at each axis on the table 4 at the point where the second dish posture teaching instruction is inputted (step a14).

Figure 12:
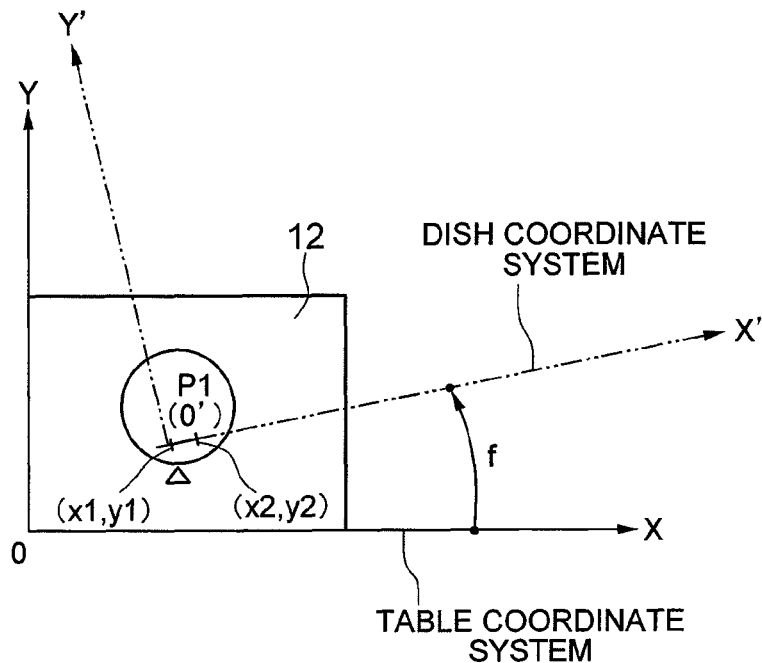
[FIG. 12] A conceptual diagram for showing the action principle of a transformation matrix which replaces a coordinate value detected on the basis of a table coordinate system into a coordinate value on a dish coordinate system.

As shown in FIG. 12, the transformation matrix f is an affine transformation matrix including a rotary movement and a parallel movement required for replacing the coordinate value that is detected on the basis of the table coordinate system into the coordinate value on the dish coordinate system. For example, the coordinate value (x1, y1) detected on the basis of the table coordinate system is replaced with the coordinate origin O' on the dish coordinate system, i.e. to the position of the first feature point P1.

Then, the CPU 18 successively selects the single cells disposed on the dish 13 and displays a message on the monitor 3d to guide the operator to register the position of the single cells (step a15), and initializes the value of the index i for designating the field of the data storage file shown in FIG. 11 to store the cell positions to 2 once (step a16). Then, after incrementing the value of the index i again by 1 (step a17), the CPU 18 comes under a standby state to wait for a manual pulse from the first operation board 3R that functions as the manual operation device of the table 4 (step a18) or to wait for a cell position teaching instruction inputted by the operator from the foot switch 3c (step a19).

Then, the operator operates again the joystick 15R or the trackball 17R of the first operation board 3R that functions as the manual operation device so as to move the table 4 on which the dish 13 is loaded on the horizontal plane, in order to set the position of one of the single cells disposed on the dish 13 at the center of the view field of the microscope 9.

The manual pulses outputted from the first operation board 3R according to the operation of the joystick 15R or the trackball 17R are detected by the CPU 18 by the processing of step a18. Upon this, the CPU 18 starts the driving devices X1 and Y1 in accordance with the inputted pulse number (step a20) to move the table 4 to the position desired by the operator.

Then, when the operator, who has captured one of the single cells at the center of the view field of the microscope 9, operates the foot switch 3c, the cell position teaching instruction is outputted from the foot switch 3c, and this signal is detected by the CPU 18 by the processing of step a19.

Upon detecting the input of the cell position teaching instruction, the CPU 18 reads the current positions of each axis on the table 4, i.e. the current position x of the first axis (X-axis) of the table coordinate system and the current position y of the second axis (Y-axis) of the table coordinate system, from the current position storage registers that correspond to the driving devices X1 and Y1 (step a21), multiplies the transformation matrix f to the coordinate value (x, y) on the basis of the table coordinate system to find the position (xi, yi) of the cell that corresponds to the coordinate value on the dish coordinate system (step a22), and registers the coordinate value (xi, yi) to the i-th field of the m-th record of the data storage file as shown in FIG. 11, based on the current values of the register m and the index i (step a23).

The identification name of the dish 13 being used currently is registered to the first field of the m-th record of the data storage file. As a result, the positions of each single cell within the currently used dish 13 are stored within the same record together with the identification name of the dish 13 that is being used.

Then, the CPU 18 displays, on the monitor 3d with dots as shown in FIG. 1, the positions (xi, yi) of the single cells that are registered with the operation of this time so as to inform the operator that the registering processing of the single cells has been completed (step a24). At this time, the registered order numbers (the values of i−2) of the registered single cells are displayed on the display section 33 of the monitor 3d. The coordinate system used for monitor display is the dish coordinate system.

Then, the CPU 18 judges whether or not a registration completion signal is inputted from the keyboard 3b through an operation of the operator (step a25). If the registration completion signal is not inputted, the CPU 18 increments the value of the index i again by 1 (step a17) and, in the same manner described above, repeatedly executes the processing of step a18-step a25.

During the course of the processing, the operator operates the joystick 15R or the trackball 17R of the first operation board 3R that functions as the manual operation device or the foot switch 3c for inputting the teaching instruction in the same manner as described above so as to successively select the single cells disposed in the dish 13 and set those at the center of the view field of the microscope 9, and registers the positions of each single cell transformed to the coordinate value of the dish coordinate system to the i-th field of the m-th record through the processing of the CPU 18.

At last, when the operator declares the end of the registering operation by operating the keyboard 3b, this signal is detected by the CPU 18 in the processing of step a25. Upon this, the CPU 18 registers the value of the index i at the point of the registration completion signal input to the second field of the m-th record as a value for specifying the registered number of the cell positions (step a26), and ends the cell position teaching processing. The cell positions are actually registered to the third field and thereafter of each record, so that the actual registered number of the cell positions is the value obtained by subtracting 2 from the value registered to the second field.

FIG. 11 illustrates the case where only m-number of identification names for the dishes 13 are registered in a file, as a way of example. However, there is no specific limit set for the registered number m of the identification names.

Through the cell position teaching processing described above, the positions of each cell can be registered always as the coordinate values of the dish coordinate system along with the identification names of the dishes 13, regardless of the position shift of the dish coordinate system with respect to the table coordinate system or a change in the posture. Therefore, even in the case of using no micro-well, it is possible to teach the positions of the individual cells properly for each dish 13 without being affected by the position or the posture of the dish 13 loaded on the table 4.

As described, in the single cell operation supporting robot 1 proposed by the Applicant of the present invention in Japanese Unexamined Patent Publication 2004-146203, the transformation matrix f for transforming the table coordinate system into the dish coordinate system is obtained by using the first, second feature points P1, P2 provided to the dish 13 that serves as a cell incubator and using the current position detecting functions at each axis of the table 4 provided to the single cell operation supporting robot 1 itself. Then, the transformation matrix f is multiplied to the positions of each cell detected on the basis of the table coordinate system to obtain the positions of each cell on the dish coordinate system, and these cell positions are registered to the file by being associated with the identification names for specifying the dish 13.

Described next is the processing operation of the case where the dish 13 that has registered the cell positions is detached and, thereafter, the same dish 13 is loaded again on the table 4 to carry out the work such as injection.

At this time, the operator starts the controller main body 3a in a playback mode thereby to let the CPU 18 execute the playback processing as illustrated in FIG. 7-FIG. 10.

In this case, it is also desirable to place the dish 13 by setting the middle point of the long segment L0 to meet the marking 14 of the incubator holder 12, as shown in FIG. 3. Practically, however, there a position shift and a posture change of some extent are to be generated.

When starting the playback processing, the CPU 18 first reads out all the identification names of the dishes 13 that are registered to the file in the past from the data storage file as in FIG. 11 and displays those on the monitor 3d, while displaying a message on the monitor 3d to let the operator select the identification name of the dish (step b1). Then, the CPU comes under a standby state to wait for the selecting operation of the identification name carried out by the operator (step b2).

Upon checking the monitor display, the operator operates the keyboard 3b to select the identification name that corresponds to the dish 13 loaded on the table 4 at this point.

Upon detecting the selecting operation of the identification name by the processing of step b2, the CPU 18 displays a message on the monitor 3d to inform that the position and the posture of the dish 13 are to be re-taught (step b3), and initialize the value of the index i for designating the register to store the positions of the feature points to 0 once (step b4). After incrementing the value of the index i again by 1 (step b5), the CPU 18 comes under a standby state to wait for a manual pulse from the first operation board 3R that functions as the manual operation device of the table 4 (step b6) or to wait for a dish posture re-teaching instruction inputted by the operator from the foot switch 3c (step b7).

The operator first operates the joystick 15R or the trackball 17R of the first operation board 3R that functions as the manual operation device so as to move the table 4 on which the dish 13 is loaded on the horizontal plane, in order to set the position of the first feature point P1 provided on the bottom face of the dish 13 at the center of the view field of the microscope 9.

The manual pulses outputted from the first operation board 3R according to the operation of the joystick 15R or the trackball 17R are detected by the CPU 18 by the processing of step b6. Upon this, the CPU 18 starts the driving devices X1 and Y1 in accordance with the inputted pulse number (step b8) to move the table 4 to the position desired by the operator.

Then, when the operator, who has captured the feature point P1 provided on the bottom face of the dish 13 at the center of the view field of the microscope 9, operates the foot switch 3c, the dish posture re-teaching instruction is outputted from the foot switch 3c, and this signal is detected by the CPU 18 by the processing of step b7.

Upon detecting the input of the dish posture re-teaching instruction, the CPU 18 reads the current positions of each axis on the table 4, i.e. the current position x of the first axis (X-axis) of the table coordinate system and the current position y of the second axis (Y-axis) of the table coordinate system, from the current position storage registers that correspond to the driving devices X1 and Y1 (step b9), and stores those values to each of the registers x1 and y1 temporarily based on the current value of the index i (step b10).

Then, the CPU 18 judges whether or not the current values of the index i have reached 2, i.e. whether or not the detecting work of the positions of the two feature points P1 and P2 have been completed (step b11). At this point, it still remains as i=1, indicating that the detecting work of the second feature point P2 has not ended yet. Therefore, the CPU 18 increments the value of the index i again by 1 (step b5) and, in the same manner described above, comes under a standby state to wait for the input of the manual pulse from the first operation board 3R (step b6), or wait for the input of the second dish posture re-teaching instruction from the foot switch 3c (step b7).

Then, the operator operates again the joystick 15R or the trackball 17R of the first operation board 3R that functions as the manual operation device so as to move the table 4 on which the dish 13 is loaded on the horizontal plane, in order to set the position of the second feature point P2 provided on the bottom face of the dish 13 at the center of the view field of the microscope 9.

The manual pulses outputted from the first operation board 3R according to the operation of the joystick 15R or the trackball 17R are detected by the CPU 18 by the processing of step b6. Upon this, the CPU 18 starts the driving devices X1 and Y1 in accordance with the inputted pulse number (step b8) to move the table 4 to the position desired by the operator.

Then, when the operator, who has captured the feature point P2 provided on the bottom face of the dish 13 at the center of the view field of the microscope 9, operates the foot switch 3c, the second dish posture re-teaching instruction is outputted from the foot switch 3c, and this signal is detected by the CPU 18 by the processing of step b7.

Upon detecting the input of the second dish posture re-teaching instruction, the CPU 18 reads the current positions of each axis on the table 4, i.e. the current position x of the first axis (X-axis) of the table coordinate system and the current position y of the second axis (Y-axis) of the table coordinate system, from the current position storage registers that correspond to the driving devices X1 and Y1 (step b9), and stores those values to each of the registers x2 and y2 temporarily based on the current value of the index i (step b10).

Then, the CPU 18 judges whether or not the current values of the index i have reached 2, i.e. whether or not the detecting work of the positions of the two feature points P1 and P2 have been completed (step b11). At this point, it has already turned as i=2, indicating that the position detecting work regarding the first feature point P1 and the second feature point P2 has ended. Therefore, the CPU 18 finds the inverse transformation matrix g for matching the first axis (X-axis) of the table coordinate system with the straight line that starts from the point (x1, y1) and passes through the point (x2, y2), based on the values of the registers x1, y1, x2, and y2, i.e. based on the position (x1, y1) at each axis on the table 4 at the point where the first dish posture re-teaching instruction is inputted, and the position (x2, y2) at each axis on the table 4 at the point where the second dish posture re-teaching instruction is inputted (step b12).

Figure 13:
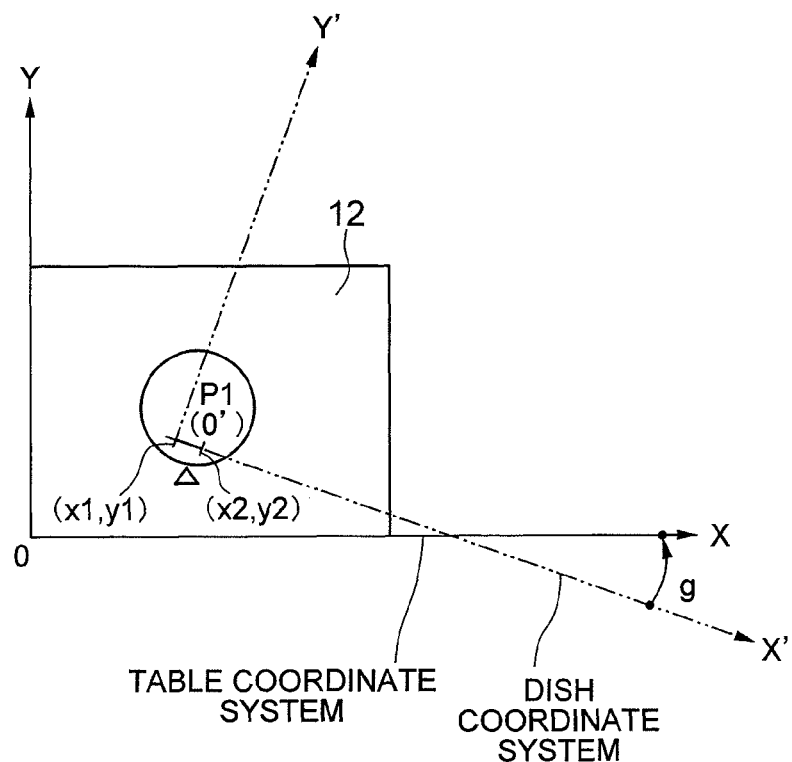
[FIG. 13] A conceptual diagram for showing the action principle of a inverse transformation matrix which replaces a coordinate value registered on the basis of the dish coordinate system into a coordinate value on the table coordinate system.

As shown in FIG. 13, the inverse transformation matrix g is an affine transformation matrix including a rotary movement and a parallel movement required for replacing the coordinate value that is registered in a file on the basis of the dish coordinate system into the coordinate value on the table coordinate system. For example, the coordinate origin O' on the dish coordinate system, i.e. the position of the first feature point P1, is replaced with the coordinate value (x1, y1) on the basis of the table coordinate system.

In general, the position and posture of the dish 13 with respect to the table 4 fluctuate every time the dish 13 is detached/attached from/to the table 4. Thus, the inverse transformation matrix g normally does not numerically match with the inverse matrix $f^{-1}$ of the transformation matrix f shown in FIG. 12. Therefore, it is useless to register and save the transformation matrix f obtained at the time of teaching operation of the cell positions or the reciprocal matrix $f^{-1}$ thereof in a file. It is necessary to carry out a re-teaching operation regarding the position and posture of the dish 13 every time the detaching/attaching work of the dish 13 is carried out.

Then, the CPU 18 searches each record of the data storage file shown in FIG. 11 to specify the value of the record address j that stores the same identification name as the identification name selected by the processing of step b2 (step b13). Assuming that "identification name 4" is selected as the identification name by the processing of step b2, the value of the record address j is specified as 4 in the case of FIG. 11.

Then, the CPU 18 initializes the value of the index i for designating the field as the readout target of the cell position to 2 once (step b14), and increments the value of the index i again by 1 (step b15). Then, the CPU 18 reads the coordinate value (xi, yi) of the single cell from the i-th field of the j-th record of the data storage file shown in FIG. 11 based on the value of the specified record address j and the current value of the index i, and displays the value on the monitor 3d with dots as shown in FIG. 1, for example (step b16). At this time, the registered order number (the value of i−2) of the read out single cell is displayed in the display section 33 of the monitor 3d.

Then, the CPU 18 judges whether or not the current value of the index i has reached the value that specifies the registered number stored in the second field of the record address j (step b17).

If the current value of the index i has not reached the value that specifies the registered number, it means that there are still remaining single cells to be displayed on the monitor 3d with dots. Therefore, the CPU 18 increments the value of the index i and repeatedly executes the same processing as described above to successively read the coordinate values (xi, yi) of the single cells registered with the dish coordinate system from the i-th field of the j-th record, and display all the values on the monitor 3d with dots (step b15-step b17). The display order of the cell positions are the same as the registered order of the cell positions carried out in the cell position teaching processing described above.

As shown in FIG. 12 and FIG. 13, the position and the posture of the dish 13 with respect to the table 4 fluctuate variously every time the dish 13 is detached/attached from/to the table 4. However, the cell positions are displayed on the monitor 3d on the basis of the dish coordinate system, so that there is no sense of uncomfortable feeling generated on the monitor display even if the loaded condition of the dish 13 is changed.

Then, the CPU 18 displays a message on the monitor 3d to let the operator select whether to execute the work such as injection to each single cell according to the registered order of the cell positions or to execute it by a free selecting operation using the monitor 3d and double-clock operation of the mouse (step b18). Then the CPU 18 comes under a standby state to wait for the selecting operation by the operator (step b19).

Here, the operator operates the keyboard 3b to select the execution either by the registered order or by the free selection.

When the registered order is selected, the judgment result of the step b20 turns out as truth. Thus, the CPU 18 first initializes the value of the index i for designating the field as the readout target of the cell position to 2 once at the data storage file shown in FIG. 11, (step b21), and comes under a standby state to wait for the input of the position setting instruction from the foot switch 3c by the operation of the operator (step b22).

When the operator operates the foot switch 3c at this time, the position setting instruction is outputted from the foot switch 3c. Upon detecting this signal, the CPU 18 increments the value of the index i by 1 (step b23).

Then, the CPU 18 reads the coordinate value (xi, yi) of the single cells registered with the dish coordinate system from the i-th field of the j-th record of the data storage file shown in FIG. 11, based on the value of the above-described record address i and the current value of the index i (step b24). Then, the CPU 18 multiplies the inverse transformation matrix g to the coordinate value (xi, yi) on the basis of the dish coordinate system to obtain the position (xp, yp) of the cell that corresponds to the coordinate value on the table coordinate system, i.e. obtain the absolute moving target position (xp, yp) that is required for setting the position of the cell by drive-controlling the table 4 according to the table coordinate system (step b25).

Further, the CPU 18 reads the current position x of the first axis (X-axis) of the table coordinate system and the current position y of the second axis (Y-axis) of the table coordinate system to find the positional deflection (incremental amount) between the target position (xp, yp) and the current position (x, y), and moves the table 4 by distributing the output of the drive pulses in accordance with the positional deflection to the axial control circuits 24, 25 of the driving devices X1, Y1 thereby to bring the cell within the view field of the microscope 9 (step b26).

Then, the CPU 18 comes under a standby state to wait for the operator to input a manual pulse from the first operation board 3R that functions as the manual operation device of the table 4 (step b27), an injection instruction from a head switch 16R (step b28), or a skip instruction from the keyboard 3b (step b29).

When the input of the manual pulse from the first operation board 3R is detected, it means that the operator further requests a delicate position adjustment even after the position is set through playback. Thus, the CPU 18 starts the driving devices X1, Y1 in accordance with the inputted pulse number (step b30) to move the table 4 to the position desired by the operator for carrying out a fine adjustment of the cell positions within the view filed of the microscope 9.

Further, when the input of the injection instruction from the head switch 16R is detected, it means that the operator desires to execute the injection work under the current state. Thus, the CPU 18 moves the capillary 11 as the end effecter of the manipulator 5 to the insertion direction (minus direction of the Z-axis), executes normal injection processing to inject a gene, a chemical, or the like to the single cell placed within the view field of the microscope 9 at this point, and retracts the capillary 11 to the retracting position thereafter (step b31). Then, the CPU 18 changes the display color of the dots of the cell displayed at the coordinate value (xi, yi) on the dish coordinate system and the display color of the characters in the display section 33 on the monitor 3d in order to inform the operator that the injection to that cell has been completed (step b32). At this time, it is possible for the operator to select the color at will upon an instruction from the keyboard 3b. Therefore, the operator can easily check the operation process and the like of the single cells on the monitor 3d with the display colors set by the operator oneself.

Furthermore, when the input of the skip instruction from the keyboard 3b is detected, it means that the injection processing for the single cell is cancelled for the operator's convenience. Thus, the CPU 18 does not execute the injection processing and shifts to the next processing.

When the injection processing is completed or cancelled, the CPU 18 judges whether or not the current value of the index i has reached the value that specifies the registered number stored in the second field of the record address j (step b33).

If the current value of the index i has not reached the value that specifies the registered number, it means that there still remains the single cell that has not received the injection processing at this point. Therefore, the CPU 18 increments the value of the index i and repeatedly executes the same processing as described above every time the operator operates the foot switch, i.e. every time the input of the position setting instruction is detected, to successively read the coordinate values (xi, yi) of the single cells registered with the dish coordinate system from the i-th field of the j-th record, transforms the coordinate value to the coordinate value on the table coordinate system, and repeatedly executes the position setting operation to each of the single cells in accordance with the registered order, or the position setting operation and the injection processing in accordance with the registered order (step b22-step b33).

Then, at the point where it is detected at last by the processing of step b33 that the current value of the index i has reached the value that specifies the registered number stored in the second field of the record address j, the whole playback processing based on the registered order is completed.

Meanwhile, when the free selection is selected in the processing of step b19, the judgment result of step b20 turns out as false. Thus, the CPU 18 comes under a standby state to wait for one of the dots on the monitor 3d showing the cell position to be double-clicked (step b34).

The operator selects the single cell to be the target of position setting by moving a graphic cursor that is associated with the mouse to meet the dot on the monitor 3d and by double-clicking the mouse of the keyboard 3b.

When the dot that corresponds to the cell desired to have the position set is double-clicked, the CPU 18 obtains the position (x', y') of the graphic cursor at the time of double-click as the coordinate value on the dish coordinate system (step b35), and sets the settable maximum value permitted by the CPU 18 in a minimum value storage register Tmin as the initial value (step b36).

Then, the CPU 18 initializes the value of the index i for designating the field as the readout target of the cell position to 2 once (step b37), and increments again the value of the index i by 1 (step b38). Then, the CPU 18 reads the coordinate value (xi, yi) of the single cell registered with the dish coordinate system from the i-th field of the j-th record of the data storage file shown in FIG. 11, based on the value of the record address j specified in the processing of step b13 and the current value of the index i (step b39). Then, the CPU 18 obtains the value T that corresponds to the positional deflection between the coordinate value (xi, yi) of the single cell and the position (x', y') of the graphic cursor at the time of double-click (step b40), and judges whether or not the value T that corresponds to the positional deflection is smaller than the value in the minimum value storage register Tmin (step b41).

At this stage, the settable maximum value is set in the minimum value storage register Tmin as the initial value, so that the judgment result of the step b40 essentially becomes truth. Thus, the CPU 18 updates and stores the value T that corresponds to the positional deflection between the coordinate value (xi, yi) of the single cell and the position (x', y') of the graphic cursor at the time of double-click in the minimum value storage register Tmin (step b42). Then, after setting the current value of the index i to an index k for specifying the single cell positioned most closely to the position of the graphic cursor (step b43), the CPU 18 judges whether or not the current value of the index i has reached value that specifies the registered number stored in the second field of the record address j (step b44).

If the current value of the index i has not reached the value that specifies the registered number, it means that there may be the coordinate value of other single cell that is closer to the position (x', y') of the graphic cursor at the time of double-click than the coordinate value (xk, yk) of the single cell that is detected at this point. Thus, the CPU 18 increments the value of the index i and repeatedly executes the same processing as described above to successively update the value i of the field where the coordinate value is stored, and store it to the index k, every time there is detected the coordinate value (xi, yi) of the single cell where the value T, which corresponds to the positional deflection between with the position (x', y') of the graphic cursor, is smaller than the value of the minimum value storage register Tmin at this point.

At the point where the judgment result of step b44 turns as false at last, the coordinate value (xk, yk) of the single cell that corresponds to the value of the index k is the coordinate of the single cell that is the closest to the position (x', y') of the graphic cursor at the time of the double-click operation.

Therefore, the CPU 18 comprehends that the single cell positioned at the coordinate value (xk, yk) is selected as the target of position setting by double-click, and reads the coordinate value (xk, yk) of the single cell registered with the dish coordinate system, i.e. reads the coordinate value (xk, yk) of the single cell that is closest to the double-clicked position, from the k-th field of the j-th record of the data storage file shown in FIG. 11 based on the value of the record address j and the current value of the index k (step b45). Then, the CPU 18 multiplies the inverse transformation matrix g to the coordinate value (xk, yk) on the basis of the dish coordinate system to obtain the position (xp, yp) of the cell that corresponds to the coordinate value on the table coordinate system, i.e. obtain the absolute moving target position (xp, yp) that is required for setting the position of the cell by drive-controlling the table 4 according to the table coordinate system (step b46).

Further, the CPU 18 reads the current position x of the first axis (X-axis) of the table coordinate system and the current position y of the second axis (Y-axis) of the table coordinate system to find the positional deflection (incremental amount) between the target position (xp, yp) and the current position (x, y), and moves the table 4 by distributing the output of the drive pulses in accordance with the positional deflection to the axial control circuits 24, 25 of the driving devices X1, Y1 thereby to bring the cell within the view field of the microscope 9 (step b47).

Then, the CPU 18 comes under a standby state to wait for the operator to input a manual pulse from the first operation board 3R that functions as the manual operation device of the table 4 (step b48), an injection instruction from a head switch 16R (step b49), or a skip instruction from the keyboard 3b (step b50).

When the input of the manual pulse from the first operation board 3R is detected, it means that the operator further requests a delicate position adjustment even after the position setting through playback. Thus, the CPU 18 starts the driving devices X1, Y1 in accordance with the inputted pulse number (step b51) to move the table 4 to the position desired by the operator for carrying out a fine adjustment on the cell positions within the view field of the microscope 9.

Further, when the input of the injection instruction from the head switch 16R is detected, it means that the operator desires to execute the injection work under the current state. Thus, the CPU 18 moves the capillary 11 as the end effecter of the manipulator 5 to the insertion direction (minus direction of the Z-axis), executes normal injection processing to inject a gene, a chemical, or the like to the single cell placed within the view field of the microscope 9 at this point, and retracts the capillary 11 to the retracting position thereafter (step b52). Then, the CPU 18 changes the display color of the dots of the cell displayed at the coordinate value (xk, yk) on the dish coordinate system and the display color of the characters in the display section 33 on the monitor 3d to inform the operator that the injection to that cell has been completed (step b53). In the same manner described above, it is possible for the operator to select the display color at will upon an instruction from the keyboard 3b. Therefore, the operator can easily check the operation process and the like of the single cells on the monitor 3d with the display colors set by the operator oneself.

Furthermore, when the input of the skip instruction from the keyboard 3b is detected, it means that the injection processing for the single cell is cancelled for the operator's convenience. Thus, the CPU 18 does not execute the injection processing and shifts to the next processing.

When the injection processing is completed or cancelled, the CPU 18 judges whether or not there is a cell operation end instruction inputted from the keyboard 3b by an operation of the operator (step b54). If the cell operation end instruction is not inputted, the CPU 18 waits for the single cell as the target of position setting to be selected again by double-clicking the dot on the monitor 3d, and repeatedly executes the same processing as described above for this single cell.

Further, when the cell operation end instruction is inputted from the keyboard 3b through the operation of the operator, it means that the operator is requesting to end the cell operation. Thus, the CPU 18 ends the whole playback processing based on the free selecting operation with the use of the monitor 3d and the double-click operation of the mouse.

In this single cell operation supporting robot 1, the cell positions registered in a file on the basis of the dish coordinate system that is the intrinsic coordinate system to the dish 13 are automatically replaced with the positions on the table coordinate system that is required for drive-controlling the table 4. Thus, the data of cell positions taught for the controller 3 in the past can be used as it is. Moreover, it is possible to set each of the registered cells on each dish 13 to fall within the view field of the microscope 9 properly and to carry out the processing operations by the manipulators 5 and 6, without being affected by the changes in the position and posture of the dish 13 that is put back on the table 4 again.

Moreover, it is possible to execute the work such as injection sequentially to each of the single cells in accordance with the registered order (the numbering order) of the cell positions or to execute it with a free selection by using the monitor 3d and a double-click operation of the mouse. Therefore, it is possible to execute the work such as injection by selecting more preferable mode depending on the circumstances of the experiments.

Further, the display color of the dot that corresponds to the cell to which the work such as injection has been executed is automatically changed on the screen of the monitor 3d. Therefore, it is possible to effectively suppress operational mistakes such as double-charging of a gene, a chemical, or the like.

As in the conventional case where injection work is carried out by finding the single cell through manually operating the joystick 15R and the trackball 17R while looking through the microscope 9, detection of the single cells itself requires a skill. Thus, there is a considerable limit set for the number of the single cells that can be actually processed. In this single cell operation supporting robot 1, however, the position setting operation for setting the target single cell to the view field of the microscope 9 is completely automated with the playback action. Thus, it is possible to reduce the work time remarkably.

The above-described case selects whether to execute the work such as injection to each of the single cells in accordance with the registered order of the cell positions or to execute it by the free selecting operation using the monitor 3*d* and the double-click operation of the mouse. However, it is also possible to constitute the structure such that, while executing the work such as injection to each of the single cells in accordance with the registered order of the cell positions, the operation is changed to the free selection using the double-click operation as necessary.

Figure 8:
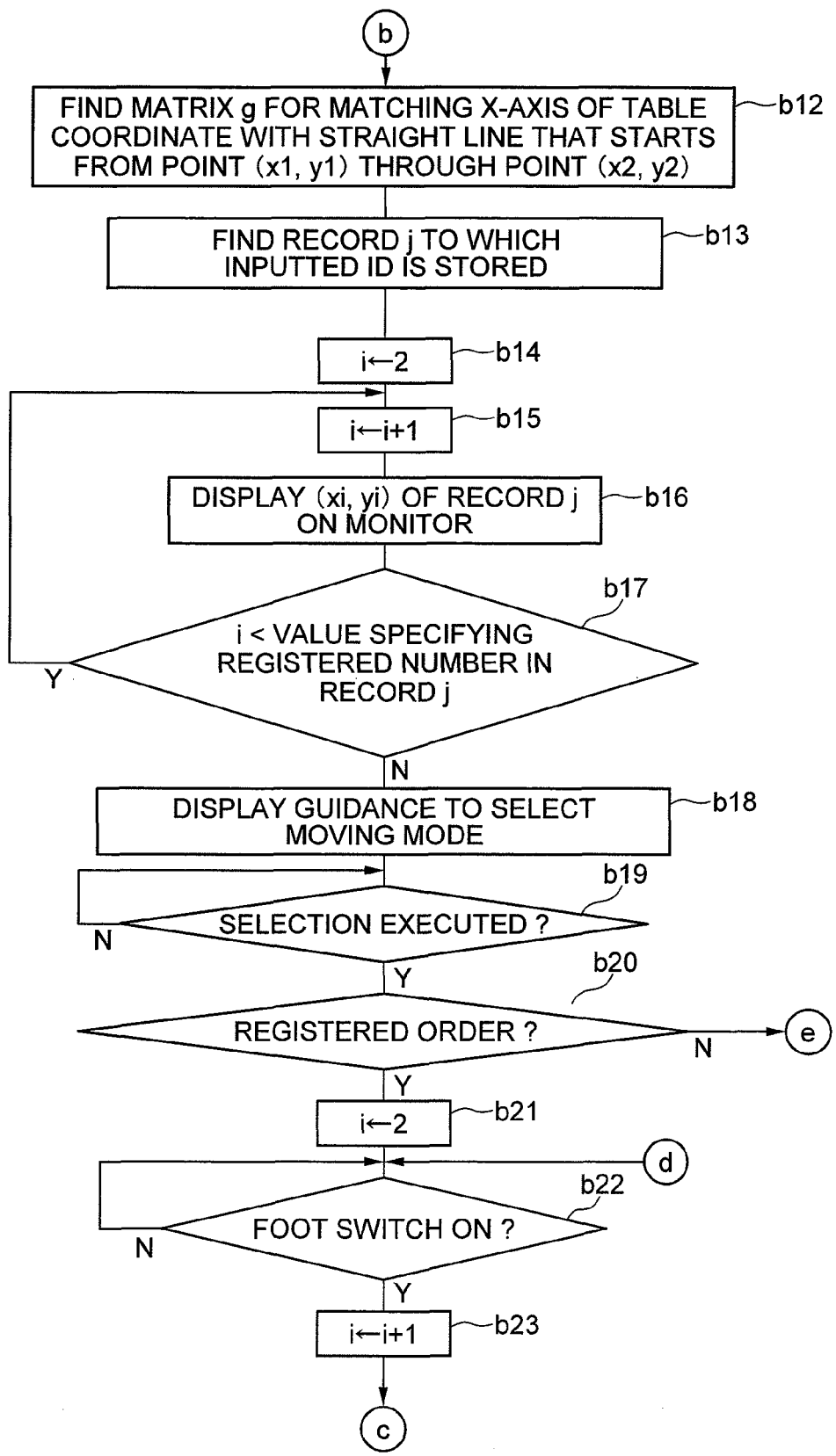
[FIG. 8] A following flowchart of the playback processing.
Figure 9:
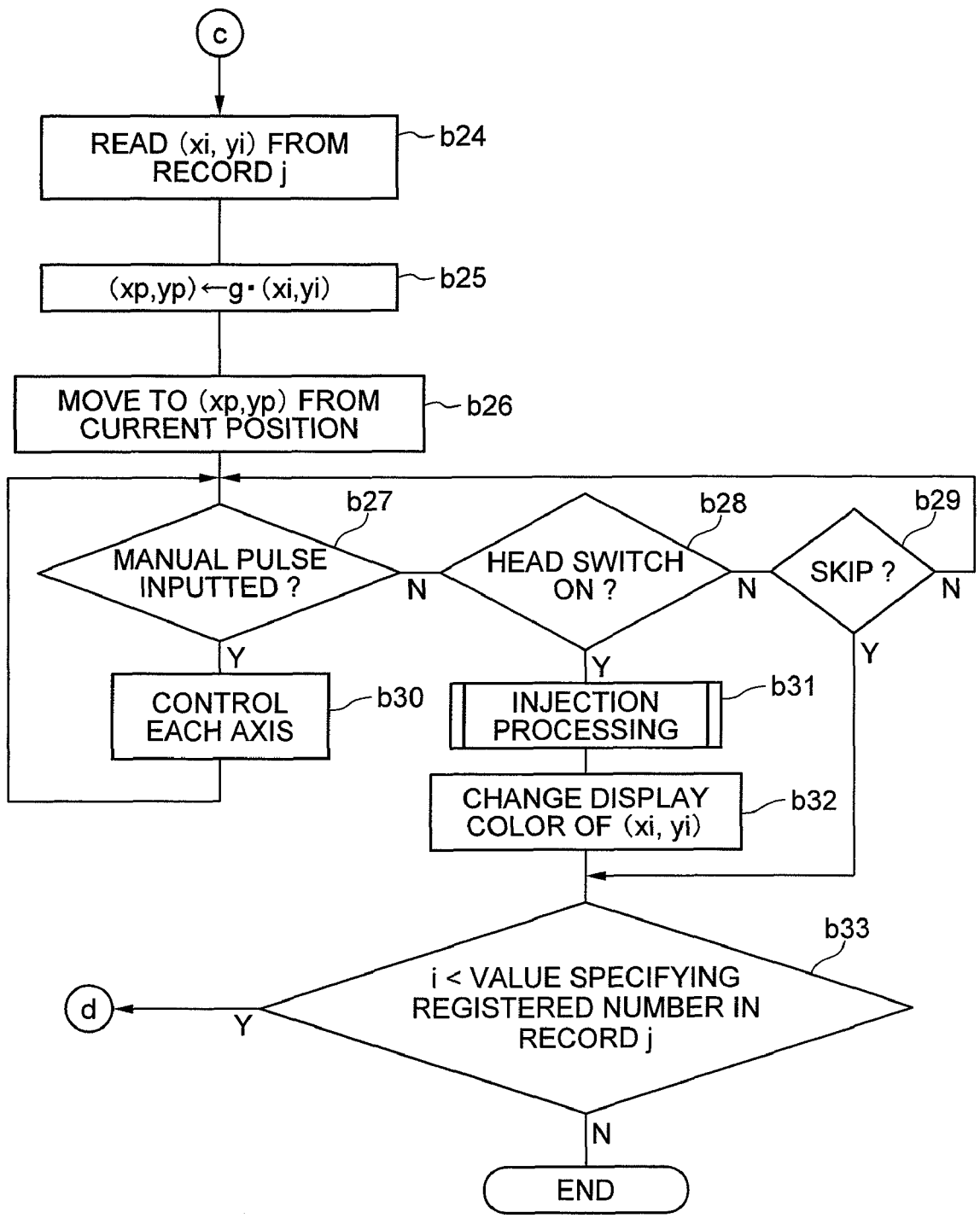
[FIG. 9] A following flowchart of the playback processing.
Figure 10:
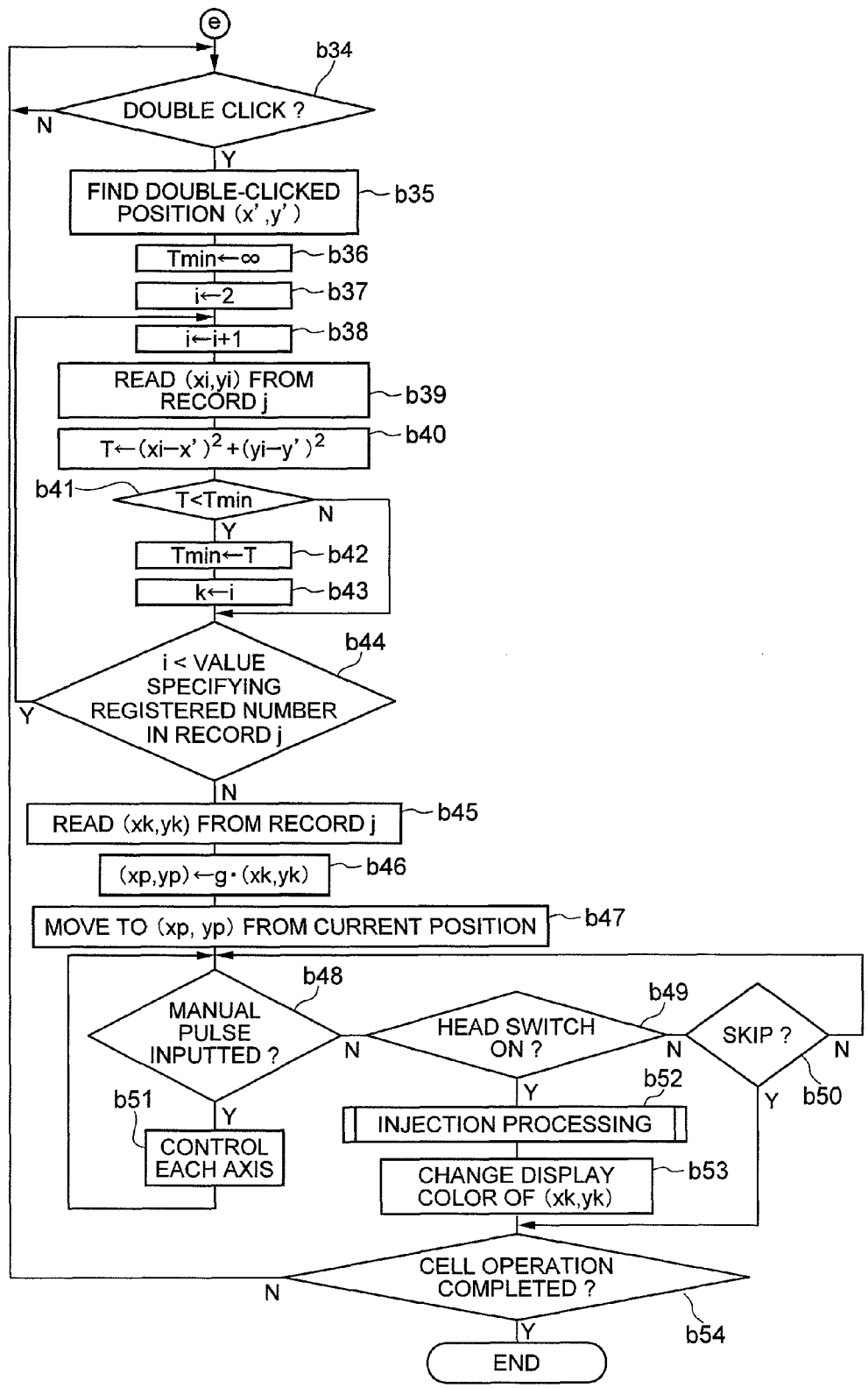
[FIG. 10] A following flowchart of the playback processing.

In this case, specifically, the processing of step b18-step b20 shown in FIG. 8 is cancelled, and when the judgment result of step b22 turns out as false, it is shifted to the processing of step b34. Further, when the judgment result of step b34 turns out as false, it is returned to the judgment processing of step b22. Meanwhile, when the judgment result of step b54 turns out as false, it is returned to the judgment processing of step b22 after substituting the value of the index k to the index i.

When such a program is created, positions of the cells are set in the view field of the microscope 9 in order in accordance with the registered order, unless there is a double-click operation. Further, when position setting by the double-click operation is executed once, the value of the index k is substituted to the index i, and the value of the index i is incremented by 1 through the operation of the foot switch 3*c* that is executed next. Thus, with the operation of the foot switch 3*c* at this time, the cell registered right after the cell that is selected by the previous double-click operation is set as the target for the position setting.

Next, there will be described a specific structural example of a cell incubator for the single cell operation supporting robot, which is the main point of the present invention.

EMBODIMENT 1

Figure 14:
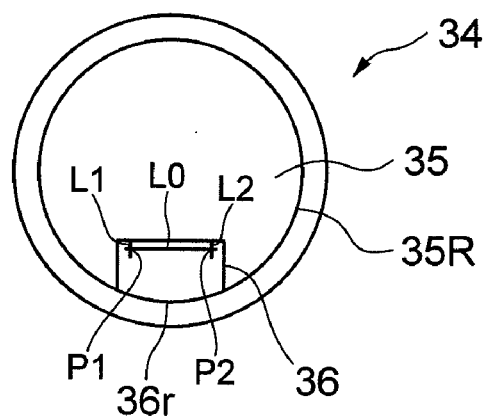
[FIG. 14] A plan view for showing an example (EMBODIMENT 1) of a cell incubator for a single cell operation supporting robot, which is constituted with a conventional-type dish that functions as a cell incubator main body for placing the cells and a feature point setup chip.

FIG. 14 is a plan view for showing the structure of a dish that is a kind of a cell incubator for a single cell operation supporting robot. This dish 34 is a cell incubator used in the single cell operation supporting robot 1 described above, which is constituted with a conventional-type dish 35 as in FIG. 15A functioning as the incubator main body for placing the cells, and a film-like or plate-like feature point setup chip 36 as in FIG. 15B where the above-described first and second feature points P1, P2 are formed. The dish 34 is formed integrally as an incubator for the single cell operation supporting robot by sticking the feature point setup chip 36 to the conventional dish 35.

The two feature points P1, P2 on the feature point setup chip 36 are formed by the intersection points between a long segment L0 and each of short segments L1, L2 which are substantially orthogonal to the long segment L0 at both ends. The long segment L0 and the short segments L1, L2 themselves are formed by using various known methods such as laser sputtering, printing, caving or the like performed on the film-like feature point setup chip 36 that is made of glass, quartz, resin, or the like. It is desirable to set the line width of the long segment L0 and the short segments L1, L2 to be 5 μm or less because of the reasons described above.

Figure 15A:
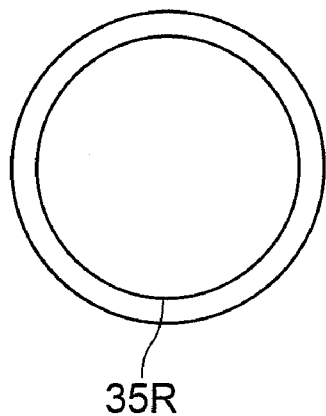
FIG. 15A shows a conventional-type dish that functions as the cell incubator main body.
Figure 15B:
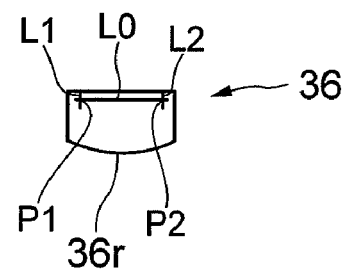
FIG. 15B shows a feature point setup chip formed in such a manner that a part of the circumferential contour matches the shape of the circumferential contour of the bottom face of the cell incubator main body (EMBODIMENT 1)

Further, as shown in FIG. 15B and FIG. 15A, a part 36*r* of the circumferential contour of the feature point setup chip 36 is formed in an arc shape to match with an arc shape 35R of the circumferential contour of the bottom face of the conventional-type dish 35 to which the feature point setup chip 36 is stuck.

As described, through forming the part 36*r* of the circumferential contour of the feature point setup chip 36 to match with the shape 35R of the circumferential contour of the bottom face of the conventional-type dish 35 that serves as the incubator main body, the position setting work of the feature point setup chip 36 becomes easy when sticking it to the conventional-type dish 35. Thus, it becomes also possible to prevent variations generated between the sticking positions of the feature point setup chips 36, when fabricating a great number of cell incubators 34 for the single cell operation supporting robot by using the same kind of conventional-type dishes 35 of the same shape and size.

It is not specified which position along the shape 35R of the circumferential contour of the bottom face of the conventional-type dish 35 the feature point setup chip 36 is to be stuck. However, the circumferential contour of the bottom face of the dish 35 is a circle, so that there is no substantial individual difference as long as the part 36*r* of the circumferential contour of the feature point setup chip 36 is stuck to the dish 35 along the shape 35R of the circumferential contour of the bottom face thereof.

On an assumption that the outer diameter of the bottom face of the conventional-type dish 35 used as the cell incubator main body is 30 mmϕ, the part 36*r* of the circumferential contour of the feature point setup chip 36 is formed in an arc shape of 30 mmϕ, and it is stuck by having the circumferential contour 36*r* matched along the circumferential contour 35R of bottom face of the conventional-type dish 35.

EMBODIMENT 2

Figure 16A:
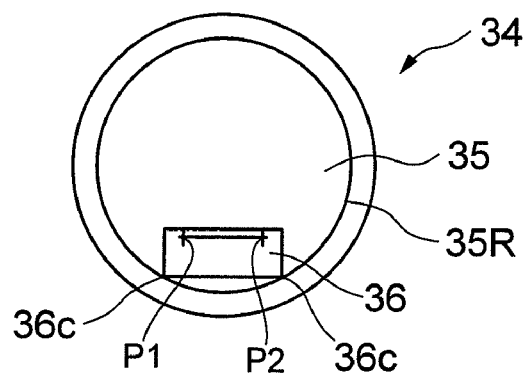
FIG. 16A shows a conventional-type dish to which the feature point setup chip is stuck.
Figure 16B:
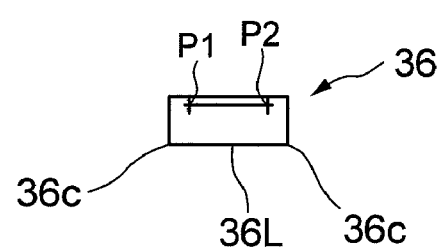
FIG. 16B shows a feature point setup chip in which a corner part is formed on both sides of a straight-line side that constitutes a part of the circumferential contour (EMBODIMENT 2)

Further, as shown in FIG. 16B, corner parts 36*c* and 36*c* may be formed on both sides of a straight-line side 36L that constitutes a part of the circumferential contour of the feature point setup chip 36.

When such structure is applied, as shown in FIG. 16A, it is possible to prevent variations generated between the sticking positions of the feature point setup chips 36, through sticking the feature point setup chip 36 to the conventional-type dish 35 while having the corner parts 36*c* and 36*c* positioned at both sides of the straight-line side 36L inscribed to the circumferential contour 35R of the bottom face of the conventional-type dish 35.

EMBODIMENT 3

Figure 17:
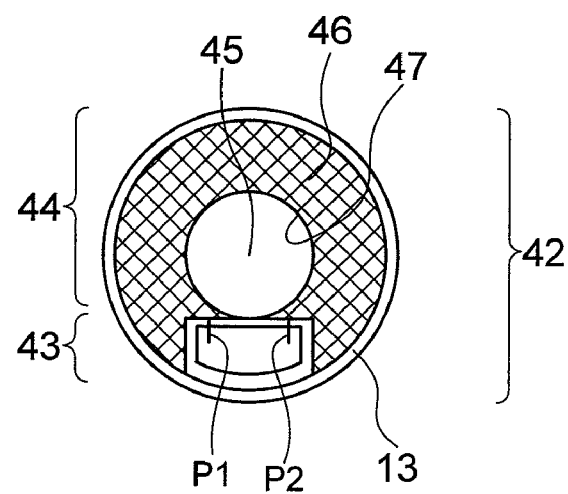
[FIG. 17] A plan view for showing an example of a feature point setup chip having a blank part where a boundary display part is provided (EMBODIMENT 3)

FIG. 17 is a plan view for showing an example of a feature point setup chip with a blank part where a boundary display part is provided. This feature point setup chip 42 is integrally formed by a feature point setup chip main body 43 and an arc-shape blank part 44 that covers a part of the bottom face of the dish 13. Among those, the feature point setup chip main body 43 part is formed transparent, and the above-described feature points P1, P2 are drawn as in FIG. 15B.

Further, regarding the blank part 44, it is formed as a masking part 46, which means a danger zone, except for a circular safe moving zone 45 positioned at the center thereof. A boundary line 47 on the inner side of the masking part 46 functions as the boundary display part.

The safe moving zone 45 may be formed by cutting out the center part of the circular blank part 44 or may be formed by making a part of the blank part 44 transparent.

The masking part 46 can be formed by a black light shield part for shielding the passage of the light, a colored semitransparent part that gives a color to the observation light from the underneath the dish 13, a mat face or opalescent part or the like, which diffuses the light. As a practical means for forming it, it is possible to use known methods such as various kinds of printing, painting, coating, sandblasting, etc.

The safe moving zone 45 is an area that corresponds to the view field of the microscope 9 within the range where the table 4 is allowed to move without causing interference between the single cell operation supporting robot 1 as well as the additional devices thereof such as the manipulators 5, 6, the capillaries 10, 11, and the dish 13 that is the cell incubator. For example, in such a case shown in FIG. 2, under the state where the tips of the capillaries 10, 11 are projected towards the inside the dish 13, it is highly possible that the tips of the capillaries 10, 11 interfere with the edge of the circular dish 13. Thus, the shape of the safe moving zone becomes almost circular.

Strictly speaking, the shape of the safe zone 45 corresponding to the case shown in FIG. 2 is a vertically-oriented substantially elliptic moving zone that is formed by a logical product of a substantially elliptic moving zone where the left-side capillary 10 projected into the inner side of the dish 13 can be moved without interfering with the peripheral wall of the dish 13 and a substantially elliptic moving zone where the right-side capillary 11 projected into the inner side of the dish 13 can be moved without interfering with the peripheral wall of the dish 13. Here, also considering the case where the dish 13 is loaded on the table 4 in a wrong posture, the substantial shape of the safe moving zone 45 is defined as a circle, having a diameter that corresponds to the minor axis of the vertically-oriented substantially elliptic zone that is formed by the logic product described above.

Therefore, in this embodiment, even under the state where the tips of the capillaries 10, 11 are projected towards the dish 13, there is no interference generated between the capillaries 10, 11 and the peripheral wall of the dish 13 as long as the safe moving zone 45 of the feature point setup chip 42 is captured within the view field of the microscope 9, no matter what kinds of manual feeding operations are applied to the table 4.

Meanwhile, when the boundary line 47 on the inner side of the masking part 46 functioning as the boundary display part enters inside the view field of the microscope 9, the tips of the capillaries 10, 11 may interfere with the peripheral wall of the dish 13. Therefore, the operator needs to stop the feed of the table 4 to that direction immediately at this point. In this embodiment, however, the diameter of the safe moving zone 45 is designed slightly smaller than the minor axis of the vertically-oriented substantially elliptic zone described above, through setting a margin on consideration over a delay in the operation of the operator, etc. Thus, practically, there is no interference generated between the tips of the capillaries 10, 11 and the peripheral wall of the dish 13, even under the state where the boundary line 47 has entered as far as the vicinity of the center area of the view field of the microscope 9. In other words, it is possible with the operator who moves the table 4 by manual control to prevent the interference between the capillaries 10, 11 and the dish 13 with a margin, through stopping the manual feed operation after confirming that the boundary line 47 has entered the view field of the microscope 9, even though there is a little delay to start this operation.

The masking part 46 itself, which means the danger zone, is not essential. For example, it is possible to form only the line of the boundary line 47 as the boundary display part with a method such as marking-off, printing, or the like.

In that case, however, it is necessary for the operator to recognize the invasion properly at the point where the boundary line 47 has entered the corner of the view field of the microscope 9, and to take a measure for preventing the interference through feeding the table 4 in the inverse direction.

If the operator who has failed to pay such an attention allows the boundary line 47 to enter the center of the view field of the microscope 9 imprudently, it becomes difficult to judge the curve direction of the boundary line 47 that is magnified by the microscope 9, i.e. difficult to judge which side of the boundary line 47 is the safe moving zone. Thus, the operator may apply an imprudent feed in a wrong direction to avoid the interference, which may cause an unexpected interference. Alternatively, there may be carried out a mis-operation such as feeding the table 4 further in the danger zone, even though the view field of the microscope 9 has gone over the boundary line 47 and entered the danger zone because an occurrence of invasion or passing of the boundary line 47 itself with respect to the view field of the microscope 9 is overlooked.

From this view point described above, it is desirable to form the boundary display part with the boundary line 47 on the inner side of the masking part 46 that clarifies the danger zone.

When such structure is applied, it is considered hardly possible to let the boundary line 47 and the masking part 46 enter as far as the center of the view field of the microscope 9, even if the operator neglects to pay an attention by a considerable amount. Even though such a phenomenon is caused, it is evident which side of the boundary line 47 the safe moving zone 45 is at (the transparent side is the safe moving zone 45). Therefore, the operator can prevent the generation of interference beforehand through applying a proper feed in the direction to avoid the interference.

Further, the technical concept regarding the boundary line (boundary display part) 47, the safe moving zone 45, and the masking part 46 can be utilized as a separate technical means to be targeted at a prevention of interference between the single cell operation supporting robot 1 as well as the additional devices thereof and the cell incubator.

FIG. 18 is a plan view for showing an example of an interference preventing chip which prevents the interference between the single cell operation supporting robot 1 as well as the additional devices thereof and the cell incubator. This interference preventing chip 48 is constituted with the circular masking part 46 that covers a part of the bottom face of the dish 13 serving as the cell incubator. The boundary line 47 on the inner side of the masking part 46 is the boundary display part. It is optional to form the safe moving zone 45 positioned on the inner side thereof either by cutting out or by making a part of the same member as that of the masking part 46 transparent.

The structures of the masking part 46 and the safe moving zone 45 are the same as those of the feature point setup chip 42 described above. Therefore, through sticking this interference preventing chip 48 to the bottom face of the dish 13, it is possible to achieve the similar effect in terms of preventing the interference among the effects of the above-described feature point setup chip 42.

Alternatively, as shown in FIG. 19A, a transparent part 49 for sticking the feature point setup chip 36 that is shown in FIG. 15B or a notch part 49 for abutting the feature point setup chip 36 may be formed in a part of the masking part 46 of the interference preventing chip 48. The interference chip 48 having the feature point setup chip 36 stuck to the transparent part 49 may be stuck to the bottom face of the dish 13 as in FIG. 19B. Alternatively, the interference chip 48 having the feature point setup chip 36 abutted against the notch part 49, and the feature point setup chip 36 may respectively be stuck to the bottom face of the dish 13 as in FIG. 19B. With this, it becomes possible to achieve the similar function as that of the feature point setup chip 42 shown in FIG. 17, regarding the improvements in the accuracy of the position setting and prevention of the interference.

EMBODIMENT 4

Figure 20:
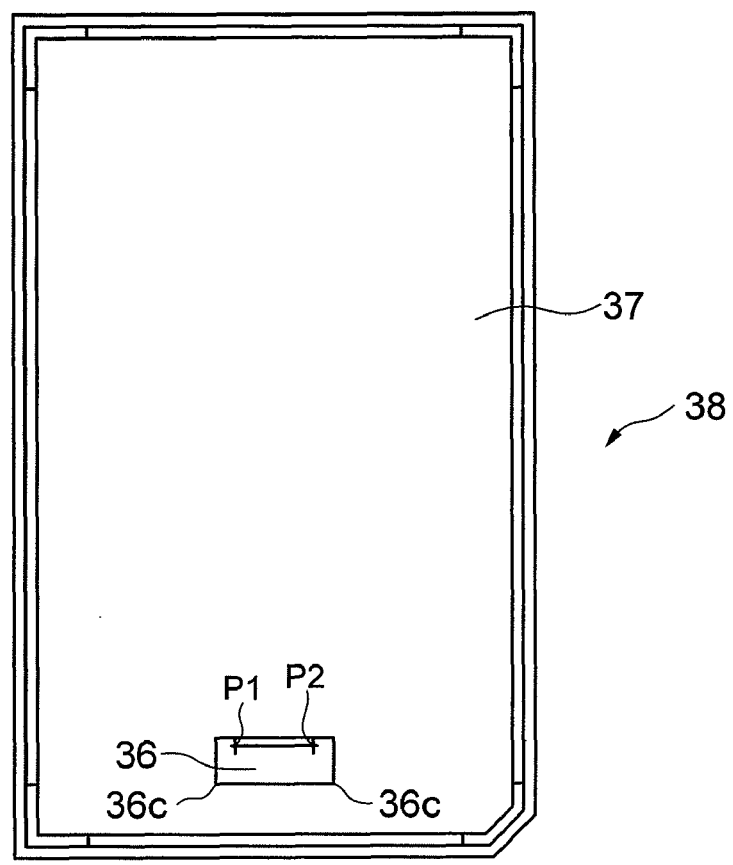
[FIG. 20] A plan view for showing an example of a cell incubator for a single cell operation supporting robot, which is constituted with a conventional-type flask plate that functions as the cell incubator main body for placing the cells, and the feature point setup chip (EMBODIMENT 4)

FIG. 20 shows an example of a cell incubator 38 for a single cell operation supporting robot, which is formed by using a conventional flask plate 37 as the cell incubator main body and by sticking the same feature point setup chip 36 as that of FIG. 16B to the bottom face of the flask plate 37.

In the case of FIG. 20, the circumferential contour of the feature point setup chip 36 does not overlap with the circumferential contour of the bottom face of the flask plate 37, and the corner parts 36c, 36c of the feature point setup chip 36 do not inscribe to the circumferential contour of the bottom face of the flask plate 37, either. In the single cell operation supporting robot 1, however, as described above, the coordinate system intrinsic to the cell incubator 38 is set by the feature points P1, P2 on the feature point setup chip 36 that is stuck to the flask plate 37 serving as the cell incubator main body, and registration of the cell positions and the playback action of the single cell operation supporting robot 1 are carried out by using this coordinate system, regardless of the shifts in the positions and postures of the cell incubator 38 and the feature point setup chip 36 generated with respect to the table 4. Therefore, even if there is a little shift generated on the position and posture of the feature point setup chip 36 with respect to the flask plate 37, it does not affect the teaching operation of the cell positions and the playback operation.

EMBODIMENT 5

Figure 21A:
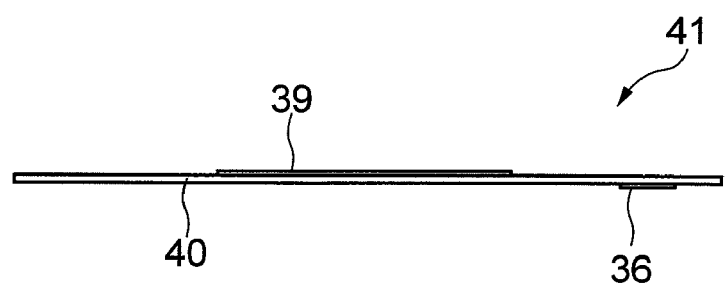
FIG. 21A is a side view of a conventional-type slide glass to which the feature point setup chip is stuck.
Figure 21B:
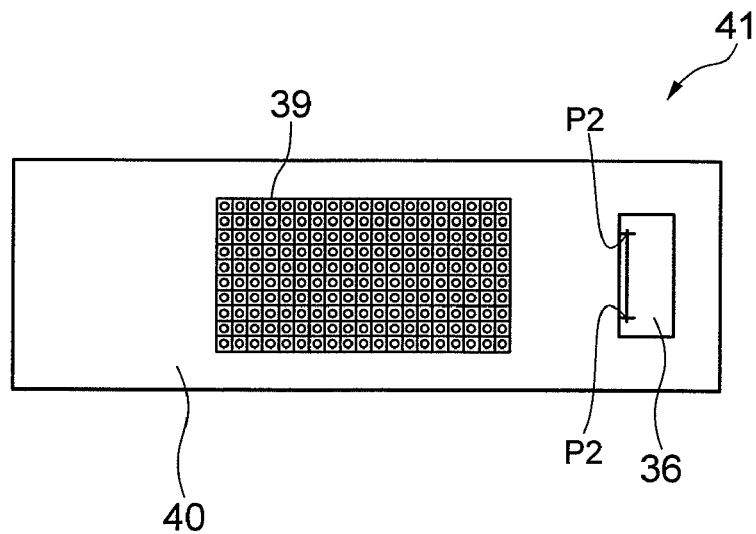
FIG. 21B is a plan view thereof (EMBODIMENT 5).

Next, a side view of FIG. 21 and a plan view of FIG. 21B illustrate the structural example of a cell incubator 41 for a single cell operation supporting robot, which is formed by using a conventional-type slide glass 40 that is provided with a well 39 for dealing with suspended cells as the cell incubator main body, and by sticking the same feature point setup chip 36 as that of FIG. 16B to the bottom face of the slide glass 40.

FIG. 21A illustrates the case where the feature point setup chip 36 is stuck on the back face side of the bottom face of the slide glass 40. However, the feature point setup chip 36 may be stuck on the top face side of the slide glass 40, i.e. on the same face as the face where the well 39 is provided.

Similarly, in the case of the dish 34 shown in FIG. 14, FIG. 16, and the flask plate 37 shown in FIG. 20, it is also possible to stick the feature point setup chip 36 selectively to either the back side or the top face side of the bottom face.

In any cases, the feature point setup chip 36 is formed with a transparent member like the cell incubator main body such as the dish 35, the flask plate 37, or the slide glass 40. However, the feature point setup chip 36 has a thickness of some extent, so that the stuck position of the feature point setup chip 36 on the cell incubator main body such as the dish 35, the flask plate 37, or the slide glass 40, i.e. the position where the first and second feature points P1 and P2 are placed, can easily be recognized visually.

Therefore, through the visual inspection, the cell incubator for the single cell operation supporting robot can be placed on the table 4 in such a manner that the positions of the first, second feature points P1, P2 come within the view field of the microscope 9 or in the vicinity thereof. As a result, it becomes unnecessary to find the feature points P1 and P2 by searching the entire bottom face of the cell incubator with the microscope 9. Thus, the preparation work time required for teaching the position/posture of the cell incubator as the prerequisite for the teaching operation of the cell positions and the playback action can be saved.

Furthermore, by utilizing the thickness of the feature point setup chip 36, it is possible to set in advance the positions of the first, second feature points P1, P2 within the view field of the microscope 9 or in the vicinity thereof by visually checking the existing position of the first, second feature points P1, P2. Therefore, the line width of the long segment L0 and the short segments L1, L2 which constitute the feature points P1, P2 can be formed as narrow as possible within a range detectable with the microscope 9. For example, it is possible to be formed as 3 μm or less, which is hard to be recognized visually. With this, the position detecting accuracy of the feature points P1, P2 and, further, the teaching accuracy of the cell positions and the position setting accuracy at the time of the playback action can be improved.

As has been described above, by constituting the cell incubator for the single cell operation supporting robot 1 through forming the first, second feature points P1, P2 on the film-like feature point setup chip 36, and sticking the feature point setup chip 36 to the cell incubator main body such as the conventional-type dish 35, flask plate 37, or the slide glass 40, it is possible to provide, at a low cost, a cell incubator for the single cell operation supporting robot 1, which is provided with the markers (the first and second feature points P1, P2) that are required for transforming the position of the cell detected on the table coordinate system into a position on the intrinsic coordinate system of the cell incubator, without fabricating a new die for forming the first, second feature points directly on the cell incubator main body.

Moreover, since various kinds of the existing dishes 35, flask plates 37, the slide glasses 40, or the like can be used as the cell incubator main bodies, users can freely select and use the accustomed cell incubator main body that has been used conventionally or various kinds of cell incubator main bodies appropriate for the objective of the experiments and the like, i.e. freely select and use various kinds of existing dishes 35, the flask plate 37, the slide glasses 40, etc.

Furthermore, in addition to the first and second feature points P1 and P2 (the long segment L0, the short segments L1, L2), a marking for detecting the feature points, which can be easily recognized visually, may be formed on the feature point setup chip 36 by a method such as printing.

The invention claimed is:

1. A cell incubator, comprising:
    a dish;
    a feature point setup chip which sticks to a bottom face of the dish; and
    a masking part which sticks to the bottom face of the dish,
    wherein the feature point setup chip comprises markings consisting of a long straight segment and two short straight segments which are substantially orthogonal to the long segment and intersect two ends of the long segment, a width of the long segment and each of the short segments being no greater than 5 μm,
    the masking part is visually distinguishable from a safe moving zone located inside the masking part when viewed under a microscope, the entire safe moving zone being transparent, and
    the feature point setup chip fits within a notch in the masking part.

2. A cell incubator according to claim 1, wherein the masking part is shaped as a ring, the safe moving zone is shaped as a circle, and the notch in the masking part has the same shape as the feature point setup chip.

* * * * *